US009645116B2

(12) United States Patent
Yoshimura et al.

(10) Patent No.: US 9,645,116 B2
(45) Date of Patent: May 9, 2017

(54) OBJECT CHARACTERISTICS MEASUREMENT APPARATUS

(71) Applicant: Japan Radio Co., Ltd., Tokyo (JP)

(72) Inventors: Naoyuki Yoshimura, Tokyo (JP); Hiromi Yatsuda, Tokyo (JP)

(73) Assignee: JAPAN RADIO CO., LTD., Tokyo (JP)

( * ) Notice: Subject to any disclaimer, the term of this patent is extended or adjusted under 35 U.S.C. 154(b) by 422 days.

(21) Appl. No.: 14/366,641

(22) PCT Filed: Dec. 14, 2012

(86) PCT No.: PCT/JP2012/082504
§ 371 (c)(1),
(2) Date: Jun. 18, 2014

(87) PCT Pub. No.: WO2013/094531
PCT Pub. Date: Jun. 27, 2013

(65) Prior Publication Data
US 2015/0000414 A1  Jan. 1, 2015

(30) Foreign Application Priority Data

Dec. 22, 2011  (JP) ................................ 2011-281603
Oct. 19, 2012  (JP) ................................ 2012-232060

(51) Int. Cl.
*G01N 29/02* (2006.01)
*G01N 29/32* (2006.01)
(Continued)

(52) U.S. Cl.
CPC .......... *G01N 29/022* (2013.01); *G01H 11/08* (2013.01); *G01N 29/036* (2013.01); *G01N 29/32* (2013.01);
(Continued)

(58) Field of Classification Search
CPC .... G01N 29/022; G01N 29/036; G01N 29/32; G01N 2291/022; G01N 2291/02818;
(Continued)

(56) References Cited

U.S. PATENT DOCUMENTS 4,767,198 A * 8/1988 Solie .................... G02F 1/33
359/305
RE32,859 E * 2/1989 Marshall ............ H03H 9/02976
310/313 D
(Continued)

FOREIGN PATENT DOCUMENTS

CN          1551495 A    12/2004
CN        101052873 A    10/2007
(Continued)

OTHER PUBLICATIONS

Office Action in Chinese Application No. 201280063121.X, dated Aug. 12, 2015.
(Continued)

*Primary Examiner* — Laura Martin
*Assistant Examiner* — Rose M Miller
(74) *Attorney, Agent, or Firm* — Nixon Peabody, LLP; Khaled Shami

(57) ABSTRACT

An object characteristics measurement apparatus of the invention includes a surface acoustic wave device. The surface acoustic wave device includes: an interdigitated electrode that is formed on a first surface on a piezoelectric substrate, excites an elastic wave, and receives reflection based on the elastic wave; a reflector that has a third surface and a fourth surface between the interdigitated electrode and a second surface orthogonal to the first surface in a propagation direction of the elastic wave; a reaction field that is formed between the interdigitated electrode and the reflector, in which the measured object is to be loaded; and a (Continued)

propagator that is formed between the reflector and the second surface.

8 Claims, 14 Drawing Sheets

(51) Int. Cl.
*G01H 11/08* (2006.01)
*G01N 29/036* (2006.01)
(52) U.S. Cl.
CPC ............ *G01N 2291/022* (2013.01); *G01N 2291/02818* (2013.01); *G01N 2291/0423* (2013.01); *G01N 2291/0426* (2013.01)
(58) Field of Classification Search
CPC ... G01N 2291/0423; G01N 2291/0426; G01H 11/08; G01H 13/00; H03H 9/02015; H03H 9/02535; H03H 9/02637; H03H 9/02566; H03H 9/02724; H03H 9/14502; H03H 9/02661; H03H 9/02771
USPC .. 73/649, 24.01, 24.06, 31.06, 54.41, 61.61, 73/61.75, 61.79, 64.53, 590; 310/313 R, 310/313 B, 313 D
See application file for complete search history.

(56) References Cited

U.S. PATENT DOCUMENTS

| | | | | |
|---|---|---|---|---|
| 5,367,216 | A * | 11/1994 | Egara | G06G 7/195 310/313 B |
| 6,731,044 | B1 * | 5/2004 | Mukai | H03H 9/02669 310/313 B |
| 2004/0222717 | A1 * | 11/2004 | Matsuda | H03H 3/08 310/313 R |

FOREIGN PATENT DOCUMENTS

| | | |
|---|---|---|
| CN | 101868916 A | 10/2010 |
| GB | 2 073 528 A | 10/1981 |
| JP | 04-196809 | 7/1992 |
| JP | 2821263 B | 11/1998 |
| JP | 3248683 B | 1/2002 |
| JP | 2003-133888 A | 5/2003 |
| JP | 3481298 B | 12/2003 |
| JP | 2004-336503 A | 11/2004 |
| JP | 2005-214713 A | 8/2005 |
| JP | 2006-258768 A | 9/2006 |
| JP | 2007-010378 A | 1/2007 |
| JP | 2007-225546 A | 9/2007 |
| JP | 2008-286606 A | 11/2008 |
| JP | 2009-281801 A | 12/2009 |
| JP | 2009-300302 A | 12/2009 |
| JP | 2010-107485 A | 5/2010 |
| WO | 2010/021100 A1 | 2/2010 |

OTHER PUBLICATIONS

Extended European Search Report in European Application No. 12860189.5, dated Aug. 20, 2015.
Hato, I. et al., Development of Novel SAW Liquid Sending System with SAW Signal Generator, Technical Report of IEICE, (Feb. 2003).
Kondo, J. et al., "Development of Surface Acoustic Wave SEnsing Suystem in Liquid", Technical Report of IEICE, 1997, pp. 1-6.
Shiokawa, S. et al., 32nd EM Symposium, Fundamental and Application of SAW Sensor, pp. 77-84.
International Search Report in PCT/JP2012/082504 dated Mar. 19, 2013.
Notice of Registration Allowance in Korean Patent Application No. 10-2014-7016588, dated Feb. 12, 2016.

* cited by examiner

OBJECT CHARACTERISTICS MEASUREMENT APPARATUS

CROSS-REFERENCE TO RELATED PATENT APPLICATION

This is the U.S. National Phase Application under 35 U.S.C. §371 of International Patent Application No. PCT/JP2012/082504 filed Dec. 14, 2012, which designated the United States and was published in a language other than English, which claims the benefit of Japanese Patent Application No. 2011-281603 filed on Dec. 22, 2011, and Japanese Patent Application No. 2012-232060 filed on Oct. 19, 2012, all of them are incorporated by reference herein. The International Application was published in Japanese on Jun. 27, 2013 as WO2013/094531 A1 under PCT Article 21(2).

BACKGROUND OF THE INVENTION

The present invention relates to an object characteristics measurement apparatus which includes a surface acoustic wave device which includes an interdigitated electrode that is formed on a piezoelectric substrate and excites a surface acoustic wave and which forms a reaction field in which a measured object is to be loaded between the interdigitated electrode and an end of the piezoelectric substrate in the propagation direction of the surface acoustic wave.

DESCRIPTION OF THE RELATED ART

Generally, the surface acoustic wave device is provided with a piezoelectric substrate, and a transmitting electrode and a receiving electrode which are constituted by comb-shaped electrode fingers provided on the piezoelectric substrate.

In the surface acoustic wave device which is configured as described above, when an electrical signal is provided to the transmitting electrode, an electric field is generated between the electrode fingers, a surface acoustic wave is excited due to a piezoelectric effect, the surface acoustic wave propagates along the piezoelectric substrate, excites the receiving electrode, and is thereby converted into an electrical signal.

Regarding such a surface acoustic wave, surface acoustic wave sensors have been researched which utilizes a shear horizontal surface acoustic wave (SH-SAW: Shear horizontal Surface Acoustic Wave) polarizing in parallel to the surface of the piezoelectric substrate and is used to carry out detection of various substances or measurement of materials properties or the like (refer to Japanese Patent No. 3481298, hereinafter referred to as Patent Document 1).

The surface acoustic wave sensor utilizes a difference in characteristics of signals which are obtained by the receiving electrode in the case where a region of the measured object that is loaded onto the piezoelectric substrate is electrically opened or short-circuited, and can determine dielectric constant and electrical conductivity which are physical characteristics of the measured object.

Additionally, in a state where an uneven structure is formed on the propagation path between the transmitting electrode and the receiving electrode which are on the piezoelectric substrate, when a measured object is load onto the recessed portion, the loaded measured object forms a quasi-coating.

By utilizing a mass load effect that the quasi-coating and the piezoelectric substrate are excited while a resonance frequency varies based on the mass of the quasi-coating, it is possible to determine the density of the measured object (refer to Japanese patent No. 3248683, hereinafter referred to as Patent Document 2).

In the surface acoustic wave sensors according to Patent Documents 1 and 2, the transmitting electrode and the receiving electrode are formed on a piezoelectric substrate; on the other hand, a surface acoustic wave sensor that is configured by one transmitting-and-receiving electrode utilizing reflection of the surface acoustic wave is known (refer to Japanese Unexamined Patent Application, First Publication No. 2009-300302, hereinafter referred to as Patent Document 3).

In the surface acoustic wave sensor, an elastic wave that is excited by the transmitting-and-receiving electrode propagates a reaction field in which a measured object is loaded, thereafter, is reflected by the end of the piezoelectric substrate, and is re-input to the transmitting-and-receiving electrode.

Based on this signal, it is possible to measure the physical characteristics of the measured object.

In this case, as a result of forming the surface acoustic wave device by one transmitting-and-receiving electrode, a downsized surface acoustic wave device can be formed.

However, an elastic wave includes a surface acoustic wave that propagates along the surface of the piezoelectric substrate and a bulk wave that propagates through the inside of the piezoelectric substrate.

In the case of the surface acoustic wave sensor configured by the structure disclosed in Patent Document 3, the elastic wave including the surface acoustic wave and the bulk wave which are excited by the transmitting-and-receiving electrode is reflected by the end of the piezoelectric substrate, and both of them are input to the transmitting-and-receiving electrode.

Consequently, since the resultant signal includes a signal based on the surface acoustic wave and a signal based on the bulk wave which are mixed together therein, there is a case where physical characteristics of the measured object cannot be determined with a high level of accuracy.

SUMMARY OF THE INVENTION

The present invention was made in order to solve a defect and has an object to provide an object characteristics measurement apparatus where the apparatus separates a signal associated with a bulk wave from a signal associated with an elastic wave and can determine physical characteristics of the measured object with a high level of accuracy based on the signal associated with surface acoustic wave.

An object characteristics measurement apparatus according to one aspect of the invention includes: a surface acoustic wave device; the surface acoustic wave device includes: an interdigitated electrode that is formed on a first surface on a piezoelectric substrate, excites an elastic wave, and receives reflection based on the elastic wave; a reflector that has a third surface and a fourth surface between the interdigitated electrode and a second surface orthogonal to the first surface of the piezoelectric substrate in a propagation direction of the elastic wave, the third surface being formed at a position different from that of the first surface in a normal direction of the first surface, the fourth surface connecting an end of the first surface, which is formed perpendicular to the normal direction of the first surface, to the third surface; a reaction field that is formed between the interdigitated electrode and the reflector, in which the measured object is to be loaded; and a propagator that is formed between the reflector and the second surface, wherein a surface acoustic wave is separated and extracted from a bulk wave, and characteristics of the measured object are determined based on the extracted surface acoustic wave, the surface acoustic wave propagating along the reaction field from the interdigitated electrode, the surface acoustic wave being reflected by the fourth surface of the reflector, the surface acoustic wave propagating along a surface of the piezoelectric substrate which is included in the elastic wave that is received by the interdigitated electrode, the bulk wave being reflected by the second surface of the piezoelectric substrate, the bulk wave propagating through an inside of the piezoelectric substrate which is included in the elastic wave that is received by the interdigitated electrode.

Moreover, in the object characteristics measurement apparatus according to one aspect of the invention, it is preferable that the reflector have a wall and a height d of the wall thereof in a direction from the surface of the piezoelectric substrate toward the inside of the piezoelectric substrate be a value satisfying a relationship represented by the following formula.

$$\lambda/2 \leq d \leq H/2$$

λ: Wavelength of the elastic wave
H: Thickness of the piezoelectric substrate

Moreover, in the object characteristics measurement apparatus according to one aspect of the invention, it is preferable that the interdigitated electrode include a plurality of electrode fingers which is N pairs of the electrode fingers (N is an integer greater than or equal to 1), and a length L2 from the fourth surface of the reflector to the end of the piezoelectric substrate be a value satisfying a relationship represented by the following formula.

$$L2 \geq N \times \lambda/2$$

λ: Wavelength of the elastic wave
N: Number of a plurality of pairs of electrode fingers constituting the interdigitated electrode Moreover, in the object characteristics measurement apparatus according to one aspect of the invention, it is preferable that the reflector have the third surface and the third surface be parallel to the first surface of the piezoelectric substrate.

Moreover, in the object characteristics measurement apparatus according to one aspect of the invention, it is preferable that the reflector have the third surface and at least one portion of the third surface be a curved surface.

Moreover, in the object characteristics measurement apparatus according to one aspect of the invention, it is preferable that the reflector have the third surface and at least one portion of the third surface be an inclined face that is inclined with respect to a normal direction of the first surface of the piezoelectric substrate at a predetermined angle.

Moreover, in the object characteristics measurement apparatus according to one aspect of the invention, it is preferable that a resin fill the reflector without protruding from the first surface of the piezoelectric substrate.

Moreover, in the object characteristics measurement apparatus according to one aspect of the invention, it is preferable that a plurality of interdigitated electrodes be formed on the piezoelectric substrate in a direction perpendicular to the propagation direction of the elastic wave, and that a plurality of reaction fields, each of which corresponds to the interdigitated electrode, be formed between each interdigitated electrode and the third surface of the reflector.

Effects of the Invention

In the object characteristics measurement apparatus according to one aspect of the invention, the surface acoustic wave propagates along the reaction field, is reflected by a reflecting surface of the reflector, and is received by the interdigitated electrode; in contrast to this, a bulk wave is transmitted to a bulk wave propagator from the reaction field, is reflected by an end of the piezoelectric substrate, and thereafter, is received by the interdigitated electrode so as to be delayed by a predetermined amount of time longer than the surface acoustic wave.

Accordingly, a signal based on the bulk wave is separated from a signal based on the elastic wave by utilizing the delay time, and a signal associated with the surface acoustic wave can be extracted therefrom.

Consequently, based on the signal associated with the surface acoustic wave, it is possible to determine physical characteristics of the measured object with a high level of accuracy.

Furthermore, as a result of forming a plurality of comb-shaped electrodes in the extending direction of the reflector and forming a plurality of reaction fields, each of which is between the comb-shaped electrode and the reflector and corresponds to the comb-shaped electrode, it is possible to simultaneously determine physical characteristics of a plurality of measured objects with a high level of accuracy.

DETAILED DESCRIPTION OF THE INVENTION

Hereinafter, an embodiment of the invention will be described with reference to drawings.

<Configuration of First Embodiment>

Figure 1A:
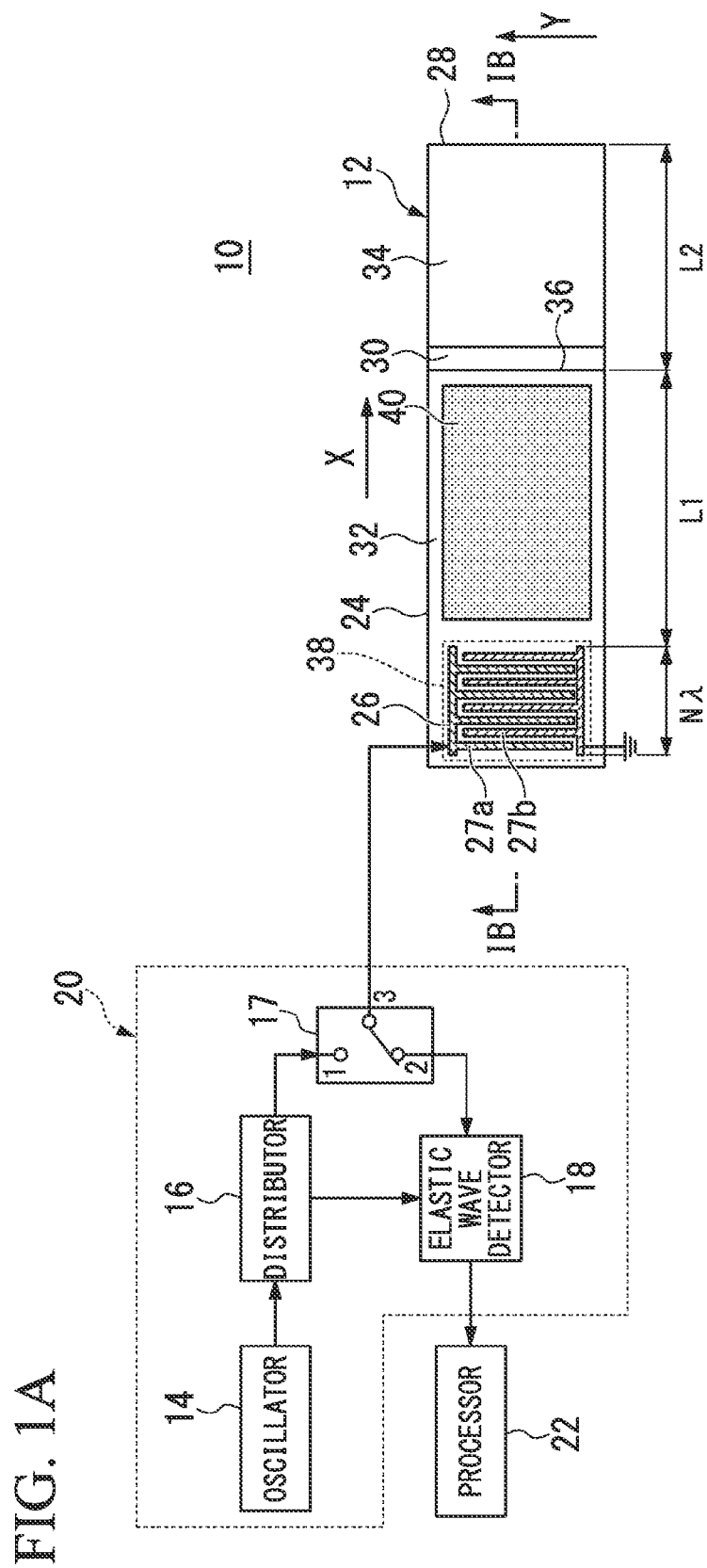
FIG. 1A is a plan view showing a configuration of an object characteristics measurement apparatus of a first embodiment of the invention including a surface acoustic wave device.
Figure 1B:
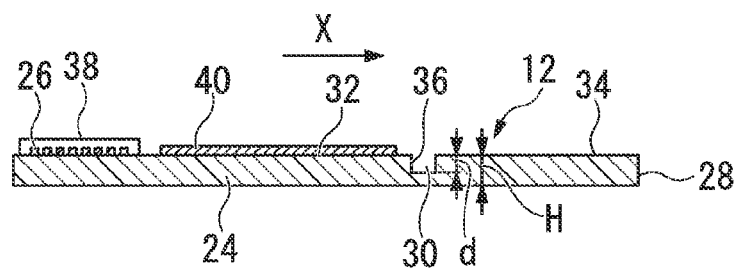
FIG. 1B is a cross-sectional view taken along the line IB-IB shown in the surface acoustic wave device shown in FIG. 1A.

FIG. 1A is a plan view showing a configuration of an object characteristics measurement apparatus of a first embodiment including a surface acoustic wave, and FIG. 1B is a cross-sectional view taken along the line IB-IB of a surface acoustic wave device shown in FIG. 1A.

The object characteristics measurement apparatus 10 measures, for example, physical characteristics of a liqui-form measured object.

The object characteristics measurement apparatus 10 includes: a surface acoustic wave device 12; a measurement unit 20 that is constituted of an oscillator 14, a distributor 16, a switch 17, and an elastic wave detector 18; and a processor 22 configured of a personal computer or the like.

The surface acoustic wave device 12 includes: a piezoelectric substrate 24; an interdigitated electrode 26 that is formed on the piezoelectric substrate 24 and excites an elastic wave; a groove (reflector) 30 that is formed between the interdigitated electrode 26 and an end 28 of the piezoelectric substrate 24 in the propagation direction of an elastic wave (the X-arrow direction); a reaction field 32 which is formed between the interdigitated electrode 26 and the groove 30 and in which the measured object is to be loaded; and a bulk wave propagator 34 (propagator) through which a bulk wave propagates and which is formed between the groove 30 and the end 28.

The elastic wave includes various kinds of wave such as a surface acoustic wave (SAW: Surface Acoustic Wave), a bulk wave, or the like.

Particularly, a surface acoustic wave is a wave that propagates along a surface of the piezoelectric substrate, and a bulk wave is a wave that propagates through the inside of the piezoelectric substrate.

Additionally, in the case where the measured object is liquid, the surface acoustic wave is a shear horizontal surface acoustic wave (SH-SAW).

In the explanation of the first embodiment, a shear horizontal surface acoustic wave is adopted as an example of the surface acoustic wave.

In the first embodiment, the shear horizontal surface acoustic wave propagates along a superficial layer portion (first surface) of the piezoelectric substrate 24, part of the shear horizontal surface acoustic wave is reflected by a reflecting surface (fourth surface) 36 of the groove (reflec-tor) 30, and the remnant of the shear horizontal surface acoustic wave passes between a bottom surface (third surface) of the groove 30 and a lower surface of the piezoelectric substrate 24 which are shown in FIG. 1B.

Additionally, a bulk wave propagates through the entire piezoelectric substrate 24, part of the bulk wave is reflected by the reflecting surface 36 of the groove 30, and the remnant of the bulk wave passes between the bottom surface of the groove 30 and the lower surface of the piezoelectric substrate 24 which are shown in FIG. 1B; and after the remnant thereof propagates through the bulk wave propagator 34, the remnant thereof is reflected by the end (second surface) 28 of the piezoelectric substrate 24.

Here, as shown in FIGS. 1A and 1B, the groove 30 has a bottom surface that is parallel to the superficial layer portion of the piezoelectric substrate 24.

As long as the piezoelectric substrate 24 has a function of capable of propagating a surface acoustic wave, a configuration of the piezoelectric substrate 24 is not particularly limited, and it is preferable to adopt 36XY-LiTaO$_3$ (lithium tantalite single crystal).

The interdigitated electrode 26 is configured so that a plurality of pairs of, that is, N pairs of electrode fingers 27a and 27b, the polarities of the electrode fingers are different from each other, and the electrode fingers are arranged in the propagation direction at a length that is equal to the wavelength $\lambda$ of the surface acoustic wave (for example, four pairs in FIG. 1A).

The interdigitated electrode 26 excites a surface acoustic wave based on a high-frequency oscillation signal (for example, center frequency is 250 MHz) generated from the oscillator 14 and causes it to propagates along the reaction field 32.

The interdigitated electrode 26 receives the shear horizontal surface acoustic wave that propagates along the reaction field 32, is reflected by the reflecting surface 36 of the groove 30, and is returned thereto through the reaction field 32.

Moreover, the interdigitated electrode 26 receives the bulk wave that transmits from the reaction field 32 to the bulk wave propagator 34, is reflected by the end 28 of the piezoelectric substrate 24, and is returned thereto through the bulk wave propagator 34 and the reaction field 32.

The interdigitated electrode 26 is tightly sealed by a sealing member 38 such as a resin or a glass in order to avoid accuracy of measurement from being degraded which is due to attachment of a measured object thereto.

The groove 30 is arrayed in the direction orthogonal to the propagation direction of the surface acoustic wave (the Y-arrow direction).

The groove 30 is formed so as to extend from one end (first substrate edge) of the piezoelectric substrate 24 to the other end (second substrate edge) in a direction orthogonal to the propagation direction of the surface acoustic wave.

The groove 30 has the reflecting surface 36 that is substantially vertical to the top surface of the piezoelectric substrate 24 along which the surface acoustic wave propagates.

As stated above, the cross-sectional configuration of the groove 30 is a projected polygonal shape such that the shape protrudes from the superficial layer portion of the piezoelectric substrate 24 toward the inside of the piezoelectric substrate 24.

In other words, the above shape, which is surrounded by the reflecting surface 36 of the groove 30, the bottom surface thereof, and the virtual line that is on the same plane as the top surface of the bulk wave propagator 34 and extends so as to close the groove 30, and is the projected polygonal shape (hereinbelow, refer to a projected polygonal shape).

In the embodiment, the cross-sectional configuration of the groove 30 is a tetragon.

The reflecting surface 36 reflects the shear horizontal surface acoustic wave to be directed to the interdigitated electrode 26.

As a depth d of the groove 30 in the direction from the top surface of the piezoelectric substrate 24 toward the inside of the piezoelectric substrate 24 (refer to FIG. 1B, a height d of a wall of the reflector), a value that satisfies the relationship of the following formula is adopted by a designer of the object characteristics measurement apparatus 10.

$$\lambda/2 \leq d \leq H/2$$

λ: Wavelength of surface acoustic wave
H: Thickness of piezoelectric substrate 24

A metal film 40 that is vapor-deposited onto the piezoelectric substrate 24 is formed the reaction field 32.

The metal film 40 forms a short-circuited propagation path which is electrically short-circuited.

The material used to form the metal film 40 is not particularly limited; however, it is preferable to use gold which is chemically stabilized with respect to a measured object which is to be dropped onto the reaction field 32.

The bulk wave propagator 34 is a region through which a bulk wave propagates; and as the length L2 from the reflecting surface 36 of the groove 30 to the end 28 of the piezoelectric substrate 24, a value that satisfies the relationship of the following formula is adopted by a designer of the object characteristics measurement apparatus 10.

$$L2 \geq N \times \lambda/2$$

λ: Wavelength of surface acoustic wave
N: Number of pairs of electrode fingers 27a and 27b.

The oscillator 14 that constitutes the measurement unit 20 produces a high-frequency oscillation signal.

The distributor 16 supplies the high-frequency oscillation signal to the interdigitated electrode 26 and the elastic wave detector 18.

The elastic wave detector 18 detects an amplitude ratio of the high-frequency oscillation signal distributed by the distributor 16 to a signal based on a surface acoustic wave which is received by the interdigitated electrode 26, a phase difference, and a propagation delay difference; and the elastic wave detector outputs, to the processor 22, a signal based on the amplitude ratio, the phase difference, and the propagation delay difference, which are detected.

The processor 22 determines the physical characteristics of the measured object based on the signal that is supplied from the elastic wave detector 18.

Moreover, the processor 22 switches between connection of the terminal 1 to the terminal 3 of the switch 17 and connection of the terminal 2 to the terminal 3 at a predetermined timing.

Particularly, physical characteristics mean, for example, the degree of viscosity, the density, or the like of a measured object.

The processor 22 determines a frequency change and a phase variation of the supplied signal in the case where, for example, nothing is dropped on the reaction field 32.

In the case where nothing is dropped on the reaction field 32, the measured object is air.

Next, a frequency change and a phase variation of the supplied signal is determined in the case where a measured object is dropped on the reaction field 32.

The processor 22 calculates two measurement data and thereby determines the degree of viscosity, the density, or the like of the dropped measured object.

<Measurement Process of First Embodiment>

The object characteristics measurement apparatus 10 according to the first embodiment is basically configured by the above.

Next, a measurement process of physical characteristics of the measured object using the object characteristics measurement apparatus 10 will be described with reference to FIGS. 1A, 1B, and 6.

Figure 6:
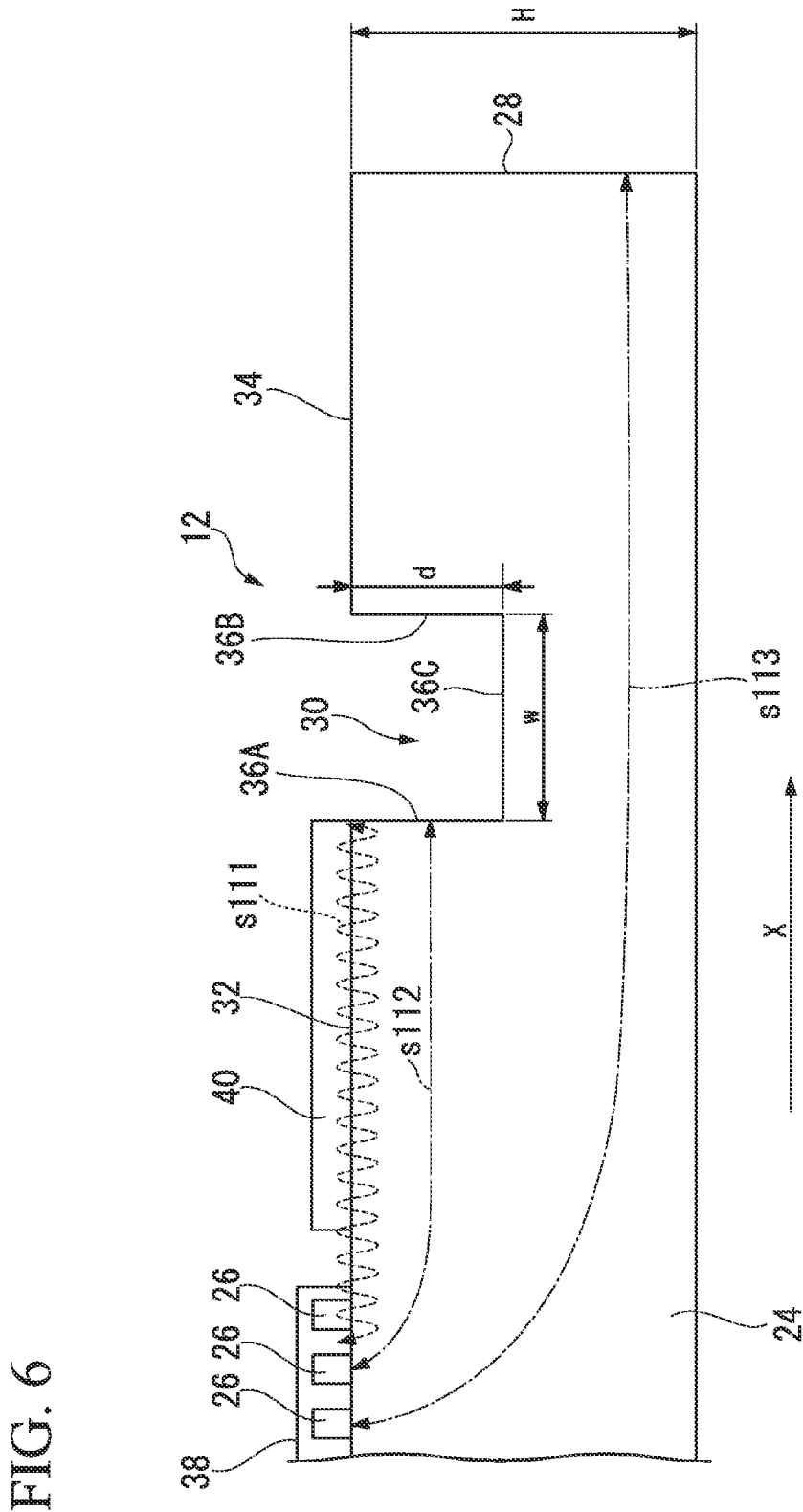
FIG. 6 is a view showing propagation of the shear horizontal surface acoustic wave signal and the bulk wave signal of the first embodiment of the invention.

FIG. 6 is a view showing propagation of the shear horizontal surface acoustic wave signal and the bulk wave signal of the first embodiment.

As similar to FIG. 1B, FIG. 6 shows part of a cross section of the surface acoustic wave device taken along the line IB-IB shown in FIG. 1A.

In FIG. 6, a curve line s111 represents a shear horizontal surface acoustic wave signal, curve lines s112 and s113 represent a bulk wave signal.

Firstly, a measurer drops a measured object onto the reaction field 32 of the surface acoustic wave device 12.

In this case, since the interdigitated electrode 26 is tightly sealed by the sealing member 38, it is possible to avoid a situation where measurement accuracy is degraded which is due to adhesion of the measured object to the interdigitated electrode 26.

Particularly, as such measured object, as long as the measured object is liquiform, for example, any of a pure liquid and a compound liquid may be adopted, and it is particularly effective to measure the physical characteristics of alcohol such as methanol or ethanol.

Moreover, even in a state where the measured object includes antigenic agent, antibody, bacteria, or the like, the physical characteristics thereof can be measured.

Next, a high-frequency oscillation signal that is burst-generated by the oscillator 14 is distributed by the distributor 16 so that the same signal is supplied to the interdigitated electrode 26 and the elastic wave detector 18.

In the interdigitated electrode 26, an elastic wave is excited in accordance with the supplied high-frequency oscillation signal.

The elastic wave propagates in the X-arrow direction along the reaction field 32 on which the measured object is dropped.

In this case, of the elastic wave propagating along the reaction field 32, a shear horizontal surface acoustic wave s111 propagates along the superficial layer portion of the piezoelectric substrate 24, part thereof is reflected by the reflecting surface 36 of the groove 30 (reflecting surface 36A (FIG. 6)), thereafter, the shear horizontal surface acoustic wave re-propagates along the reaction field 32 and is received by the interdigitated electrode 26.

Moreover, of the elastic wave propagating along the reaction field 32, the bulk waves (s112 and s113) are entirely transmitted to the piezoelectric substrate 24, as shown in FIG. 6, part thereof (s113) passes between the bottom surface of the groove 30 and the lower surface of the piezoelectric substrate 24, propagates through the bulk wave propagator 34, and reaches the end 28 of the piezoelectric substrate 24.

Subsequently, the bulk wave s113 is reflected by the end 28, thereafter, re-propagates through the bulk wave propagator 34 and the reaction field 32, and is received by the interdigitated electrode 26.

Here, in order to detect the shear horizontal surface acoustic wave with a high level of accuracy, a designer of the object characteristics measurement apparatus 10 selects a depth d of the groove 30 as described below.

The shear horizontal surface acoustic wave is a wave propagating along the superficial layer portion of the piezoelectric substrate 24.

Accordingly, as a result of determining the depth d of the groove 30 to be a value satisfying the relationship of the following formula (1), the surface acoustic wave device 12 can allow 50% or more of the shear horizontal surface acoustic wave to be reflected by the reflecting surface 36 of the groove 30 and to be received by the interdigitated electrode 26.

$$\lambda/2 \leq d \tag{1}$$

$\lambda$: Wavelength of elastic wave

On the other hand, the bulk wave is a wave propagating through the entire piezoelectric substrate 24.

Accordingly, as a result of determining the depth d of the groove 30 to be a value satisfying the relationship of the following formula (2) such as being less than or equal to half of the thickness H of the piezoelectric substrate 24, the surface acoustic wave device 12 reduces the degree of reflection of bulk wave, which is due to the reflecting surface 36 of the groove 30, to be 50% or less and can cause the residual bulk wave to transmit to the bulk propagator 34 through between the bottom surface of the groove 30 and the lower surface of the piezoelectric substrate 24.

$$d \leq H/2 \tag{2}$$

Consequently, in order to detect the shear horizontal surface acoustic wave that is to be reflected by the reflecting surface 36 of the groove 30 with a high level of accuracy, with reference to the formulas (1) and (2), the designer determines the depth d of the groove to be a value satisfying the relationship of the following formula.

$$\lambda/2 \leq d \leq H/2 \tag{3}$$

Furthermore, in order to detect the shear horizontal surface acoustic wave that is reflected by the reflecting surface 36 of the groove 30 and the bulk wave that propagates through the bulk wave propagator 34 and is reflected by the end 28 of the piezoelectric substrate 24 so that they are separated in time, the designer determines the length L2 of the bulk wave propagator 34 as described below.

Particularly, the electrode fingers 27a and 27b constitute the interdigitated electrode 26, form a plurality of pairs, and have different polarities, and the length of the electrode fingers is a wavelength $\lambda$ of the elastic wave. Where the number of pairs of the electrode fingers 27a and 27b is defined as N, the width of the interdigitated electrode 26 is represented by (N×$\lambda$) (here, N is an integer greater than or equal to 1).

In order to reliably separate the shear horizontal surface acoustic wave from the bulk wave, the designer determines a time difference (t2 −t1) to be a value satisfying the relationship of the following formula (4) where the t1 is time from when the shear horizontal surface acoustic wave is reflected by the reflecting surface 36 of the groove 30 till when the shear horizontal surface acoustic wave returns to the interdigitated electrode 26 and the t2 is time from when the bulk wave is reflected by the end 28 of the piezoelectric substrate 24 till when the bulk wave returns to the interdigitated electrode 26.

$$t2-t1 \geq N \times \lambda/v \tag{4}$$

v: Propagation velocity of elastic wave

The time difference (t2−t1) is the time required for going-forth-and-back of the bulk wave in the propagator 36 having the length L2, therefore is represented by the following formula (5).

$$t2-t1=2 \times L2/v \tag{5}$$

Consequently, in order to timewise separate the bulk wave from the received elastic wave and accurately detect the shear horizontal surface acoustic wave, the designer determines the length L2 of the propagator 36 based on the formulas (4) and (5) to be a value satisfying the relationship of the following formula (6).

$$L2 \geq N \times \lambda/2 \tag{6}$$

The shear horizontal surface acoustic wave and the bulk wave which are received by the interdigitated electrode 26 are converted into a shear horizontal surface acoustic wave signal and a bulk wave signal, thereafter, is supplied to the elastic wave detector 18.

Figure 2:
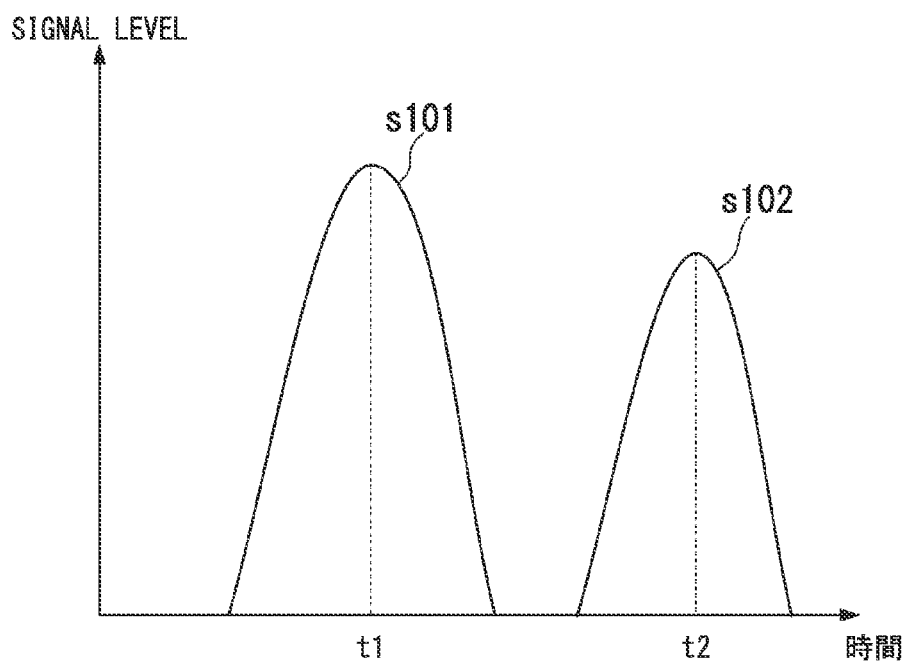
FIG. 2 is a diagram showing a relationship between the time when a shear horizontal surface acoustic wave signal and a bulk wave signal are received by an interdigitated electrode of the surface acoustic wave device of the first embodiment of the invention, and signal levels thereof.

FIG. 2 is a diagram showing a relationship between the time when a shear horizontal surface acoustic wave signal and a bulk wave signal are received by the interdigitated electrode 26 of the surface acoustic wave device 12 of the first embodiment, and signal levels thereof.

In FIG. 2, the horizontal axis represents time and the vertical axis represents a signal level.

The elastic wave detector 18 detects an amplitude ratio of a high-frequency oscillation signal that is supplied from the distributor 16 to the received signal, a phase difference, and a propagation delay difference, and outputs a signal based on the detected amplitude ratio, the detected phase difference, and the detected propagation delay difference to the processor 22.

Of such signals supplied from the elastic wave detector 18, the processor 22 separates the bulk wave signal which is delayed by a predetermined amount of time with respect to the shear horizontal surface acoustic wave signal and determines the physical characteristics of the measured object based on the signal associated with the shear horizontal surface acoustic wave.

In FIG. 2, the separated signal s101 having the center located at time t1 is a shear horizontal surface acoustic wave signal, and the separated signal s102 having the center located at time t2 that is delayed later than the shear horizontal surface acoustic wave signal is a bulk wave signal.

As mentioned above, the object characteristics measurement apparatus 10, which includes the surface acoustic wave device 12 of the first embodiment, is configured so that: a shear horizontal surface acoustic wave propagates along the reaction field 32, is reflected by the reflecting surface 36 of the groove (reflector) 30, and thereafter, is input to the interdigitated electrode 26; a bulk wave passes through the bottom of the groove 30 from the reaction field 32 and propagates through the bulk wave propagator 34, is reflected by the end 28 of the piezoelectric substrate 24, and thereafter, is input to the interdigitated electrode 26; and a predetermined time difference occurs between the shear horizontal surface acoustic wave and the bulk wave.

For this reason, the processor 22 can separate, from the signal supplied from the elastic wave detector 18, a signal based on the supplied bulk wave that is delayed by a predetermined amount of time with respect to the signal based on the shear horizontal surface acoustic wave.

As a result, based on the signal associated with the shear horizontal surface acoustic wave, the processor 22 can determine physical characteristics of the measured object that is dropped on the reaction field 32 with a high level of accuracy.

Moreover, the surface acoustic wave device 12 is configured to allow the shear horizontal surface acoustic wave to be reflected by the reflecting surface 36 of the groove 30 and to go and return, in contrast, allow the bulk wave to be reflected by the end 28 of the piezoelectric substrate 24 and to go and return, and thereby detect the shear horizontal surface acoustic wave and the bulk wave by use of a single interdigitated electrode 26.

Consequently, the object characteristics measurement apparatus 10 can be obtained which includes a downsized and inexpensive surface acoustic wave device 12 that can determine physical characteristics of the measured object with a high level of accuracy.

Figure 3:
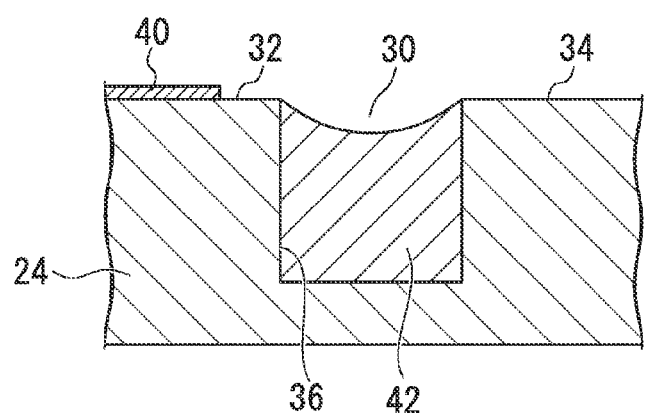
FIG. 3 is an enlarged cross-sectional view partially showing a modified example of a groove that is formed in the surface acoustic wave device of the first embodiment of the invention.

FIG. 3 is an enlarged cross-sectional view partially showing a modified example of the groove 30 that is formed in the surface acoustic wave device 12 of the first embodiment.

As similar to FIG. 1B, FIG. 3 shows part of a cross section of the surface acoustic wave device taken along the line IB-IB shown in FIG. 1A.

A resin 42, for example, epoxy resin fills the groove 30 without protruding from the top surface of the piezoelectric substrate 24.

Particularly, a depth of the groove 30 satisfies formula (3) in FIG. 3.

In such a configuration, it is possible to reduce variation in an acoustic (characteristic) impedance with respect to the shear horizontal surface acoustic wave which is due to the reflecting surface 36 of the groove 30.

That is, in the case where the groove 30 is not filled with the resin 42 and an air space exists in the groove 30, when a liquiform measured object is dropped on the groove 30, the acoustic (characteristic) impedance of the reflecting surface 36 significantly varies.

Because of this, when such measured object is dropped on the groove 30, a signal level detected by the interdigitated electrode 26 also significantly varies, and there is a concern that measurement error increases.

In contrast, in the case where part of the groove 30 is filled with the resin 42, even where a situation occurs such that part of the measured object is dropped on the groove 30, variation in the acoustic (characteristic) impedance of the reflecting surface 36 is small.

Therefore, it is possible to avoid a situation where a signal level detected by the interdigitated electrode 26 varies depending on a dropping state of a measured object.

As a result, it is possible to stably determine physical characteristics of the measured object with a high level of accuracy.

In particular, as a result of filling the groove 30 with the resin 42 so that the resin 42 does not protrude from the top surface of the piezoelectric substrate 24, even in the case where a measured object is dropped on the resin 42 inside the groove 30, effect on the shear horizontal surface acoustic wave that is reflected by the reflecting surface 36 of the groove 30 is low.

As a result, it is possible to determine physical characteristics of the measured object with a high level of accuracy.

<Configuration of Second Embodiment>

Figure 4:
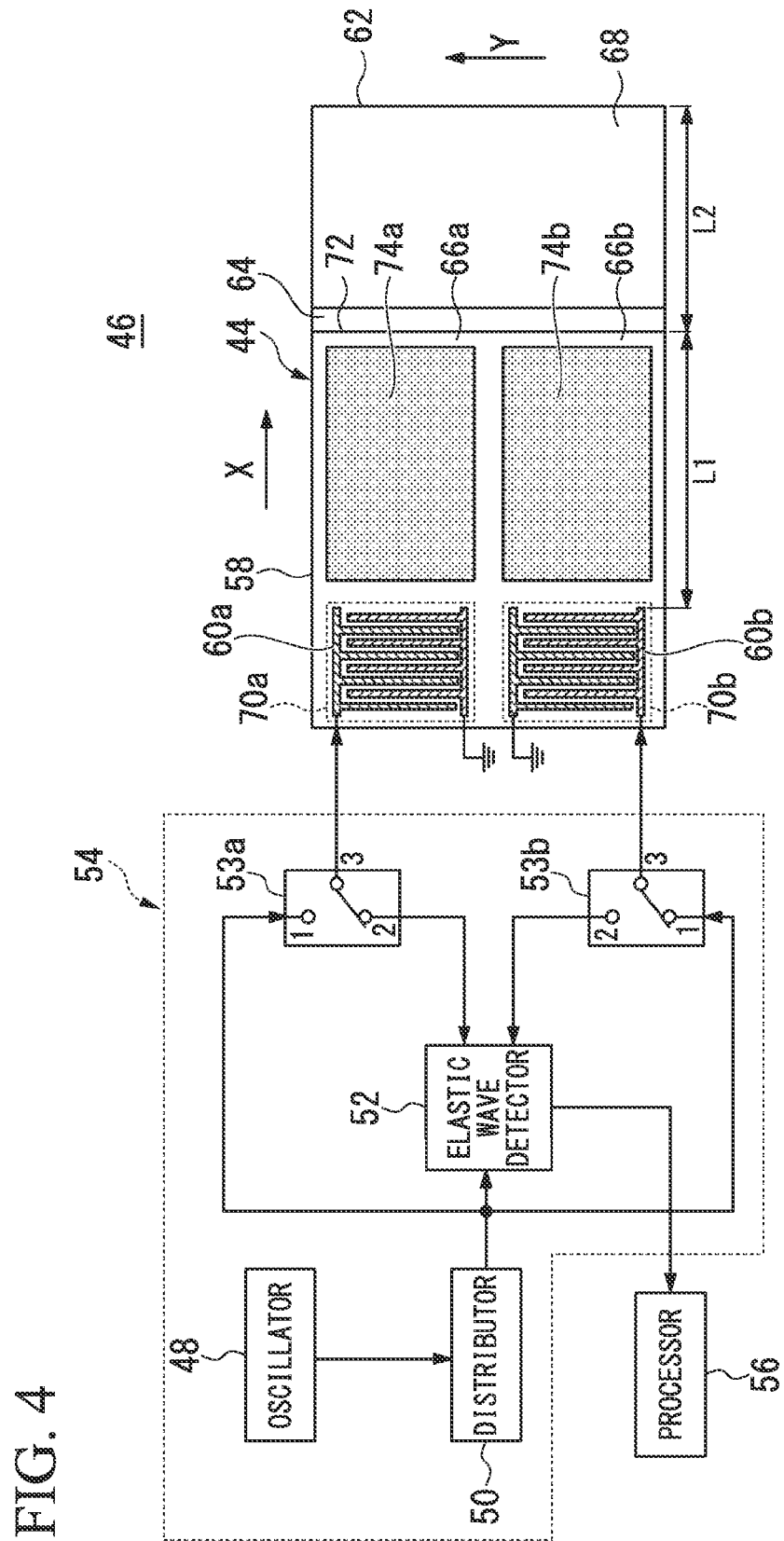
FIG. 4 is a plan view showing a configuration of an object characteristics measurement apparatus of a second embodiment of the invention including a surface acoustic wave device.

FIG. 4 is a plan view showing a configuration of an object characteristics measurement apparatus 46 of a second embodiment including a surface acoustic wave device 44.

Moreover, a constituent material of the surface acoustic wave device 44 is similar to the surface acoustic wave device 12 of the first embodiment.

The object characteristics measurement apparatus 46 includes: the surface acoustic wave device 44, an oscillator 48, a distributor 50, an elastic wave detector 52, a measurement unit 54 constituted of switches 53a and 53b, a processor 56.

Additionally, the processor 56 carries out switching of connections between the terminals 1 and 3 or between the terminals 2 and 3 of the switches 53a and 53b.

The surface acoustic wave device 44 includes: two interdigitated electrodes formed on a piezoelectric substrate 58 (first surface); a groove (reflector) 64 that is formed between the interdigitated electrode 60a and an end (second surface) 62 of the piezoelectric substrate 58 and between the interdigitated electrode 60b and the end 62; reaction fields 66a and 66b that are formed between the interdigitated electrode 60a and the groove 64 and between the interdigitated electrode 60b and the groove 64 so as to correspond to the interdigitated electrodes 60a and 60b, respectively; and a bulk wave propagator 68 that is formed between the groove 64 and the end 62.

Two interdigitated electrodes 60a and 60b are provided in parallel to each other and in a longitudinal direction of the groove 64 (the Y-arrow direction) and are tightly sealed by sealing members 70a and 70b such as a resin or a glass similar to the interdigitated electrode 26 (refer to FIGS. 1A and 1B).

Particularly, each of the interdigitated electrodes 60a and 60b corresponds to the interdigitated electrode 26 shown in FIGS. 1A and 1B and includes a plurality of pairs of electrode fingers. The pairs of the electrode fingers correspond to the pairs of the electrode fingers 27a and 27b that have polarities different from each other.

The groove 64 is formed between the each of two interdigitated electrodes 60a and 60b and the end 62 of the piezoelectric substrate 58 in the propagation direction (the X-arrow direction) of the surface acoustic wave, and a reflecting surface (fourth surface) 72 corresponding to the reflecting surface 36 is formed therein.

Furthermore, the cross section of the groove 64 is the same as that of FIG. 1B as an example, a depth of the groove is represented by reference letter d.

The depth of the groove 30 satisfies formula (3).

The reaction fields 66a and 66b are formed between the interdigitated electrode 60a and the groove 64 and between the interdigitated electrode 60b and the groove 64 so as to correspond to the interdigitated electrodes 60a and 60b, respectively.

A metal films 74a and 74b that are vapor-deposited onto the piezoelectric substrate 58 is formed the reaction fields 66a and 66b, respectively.

The bulk wave propagator 68 which is the same as the bulk wave propagator 34 (refer to FIGS. 1A and 1B) is formed between the groove 64 and the end 62.

The oscillator 48 that constitutes the measurement unit 54 produces a high-frequency oscillation signal.

The distributor 50 supplies the high-frequency oscillation signal to each of the interdigitated electrodes 60a and 60b and the elastic wave detector 52.

The elastic wave detector 52 detects an amplitude ratio of the high-frequency oscillation signal distributed by the distributor 50 to a signal based on a surface acoustic wave which is received by each of the interdigitated electrode 60a and 60b, a phase difference, and a propagation delay difference; and the elastic wave detector outputs, to the processor 56, a signal based on the amplitude ratio, the phase difference, and the propagation delay difference, which are detected.

Based on the signal that is supplied from the elastic wave detector 52, the processor 56 determines the physical characteristics of the measured object which are dropped on each of the reaction fields 66a and 66b.

As described above, in the object characteristics measurement apparatus 46 of the second embodiment, a first pair (the interdigitated electrode 60a and the reaction field 66a) and a second pair (the interdigitated electrode 60b and the reaction field 66b) are positioned in parallel with each other so that the propagation direction is parallel to the X-direction.

<Measurement Process of Second Embodiment>

In the measurement apparatus 46 according to the second embodiment which is configured as described above, it is possible to measure the physical characteristics of the measured object that is dropped on each of the reaction fields 66a and 66b in a way similar to the case of the measurement apparatus 10 according to the first embodiment.

Particularly, a high-frequency oscillation signal generated from the oscillator 48 is distributed by the distributor 50 and is supplied to each of the interdigitated electrodes 60a and 60b of the surface acoustic wave device 44 and the elastic wave detector 52 of the measurement unit 54.

In the interdigitated electrode 60a, an elastic wave is excited in accordance with the supplied high-frequency oscillation signal, the shear horizontal surface acoustic wave propagates in the X-arrow direction along the reaction field 66a on which the measured object is dropped, and thereafter, reaches a reflecting surface 72.

Subsequently, the shear horizontal surface acoustic wave is reflected by the reflecting surface 72, re-propagates along the reaction field 66a, and is received by the interdigitated electrode 60a.

The shear horizontal surface acoustic wave that is excited by the interdigitated electrode 60b is similar to the above-described embodiment.

Additionally, a bulk wave that is excited by the interdigitated electrode 60a propagates through the bulk wave propagator 68 from the reaction field 66a and reaches the end 62.

Subsequently, the bulk wave is reflected by the end 62, re-propagates through the bulk wave propagator 68 and the reaction field 66a, and is received by the interdigitated electrode 60a.

The bulk wave that is excited by the interdigitated electrode 60b is similar to the above-described embodiment.

The shear horizontal surface acoustic wave and the bulk wave which are received by each of the interdigitated electrodes 60a and 60b are converted into a shear horizontal surface acoustic wave signal and a bulk wave signal, thereafter, is supplied to the elastic wave detector 52.

The elastic wave detector 52 detects an amplitude ratio of a high-frequency oscillation signal that is supplied from the distributor 50 to the received signal, a phase difference, and a propagation delay difference, and outputs a signal based on the detected amplitude ratio and the detected phase difference to the processor 56.

Of such signals supplied from the elastic wave detector 52, the processor 56 separates the signal associated with the bulk wave which is delayed by a predetermined amount of time with respect to the signal associated with the shear horizontal surface acoustic wave, and determines the physical characteristics of the measured objects, which are dropped on the respective reaction fields 66a and 66b, based on the obtained signal associated with the shear horizontal surface acoustic wave.

In the object characteristics measurement apparatus 46 of the second embodiment which is configured as described above, in a way similar to the case of the object characteristics measurement apparatus 10 according to the first embodiment, the signal associated with the bulk wave is separated from the signal associated with the surface acoustic wave, and it is possible to determine the physical characteristics of the measured objects which are dropped on the respective reaction fields 66a and 66b based on the signal associated with the shear horizontal surface acoustic wave.

That is, in the object characteristics measurement apparatus 46, it is possible to simultaneously determine the physical characteristics of the measured objects, which are the same as each other or different from each other, with a high level of accuracy.

Moreover, in the object characteristics measurement apparatus 46 including the surface acoustic wave device 44, the physical characteristics of the measured objects which are dropped on the respective reaction fields 66a and 66b can be simultaneously determined.

Furthermore, in the case of dropping a measured object onto one reaction field 66a and processing a shear horizontal surface acoustic wave signal that is detected by each of the interdigitated electrodes 60a and 60b, the influence of variation in ambient conditions of the surface acoustic wave device 44 such as temperature change is compensated for, and it is also possible to determine the physical characteristics of the measured object with a high level of accuracy.

<Third Embodiment>

Figure 5:
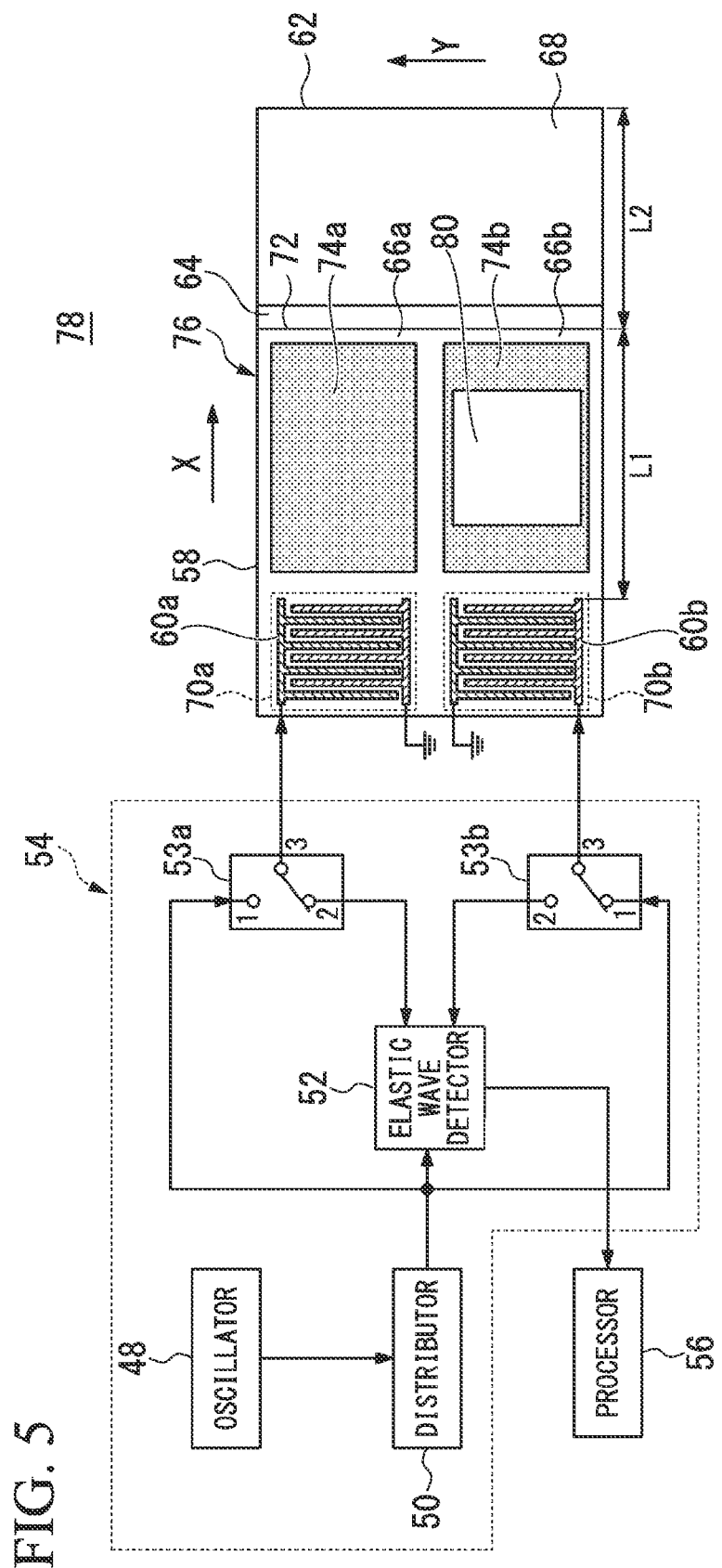
FIG. 5 is a plan view showing a configuration of an object characteristics measurement apparatus of a third embodiment of the invention including a surface acoustic wave device.

FIG. 5 is a plan view showing a configuration of an object characteristics measurement apparatus 78 of a third embodiment including a surface acoustic wave device 76.

In particular, identical reference numerals are used for constituent elements which are identical to those of the second embodiment, and the explanations thereof are omitted here.

Moreover, a constituent material of the surface acoustic wave device 76 is similar to the surface acoustic wave device 12 of the first embodiment.

Furthermore, the cross section of the groove 64 is the same as that of FIG. 1B as an example, a depth of the groove is represented by reference letter d.

The depth of the groove 30 satisfies formula (3).

As shown in FIG. 5, the surface acoustic wave device 76 includes a peeled portion 80 in which part of a metal film 74b of the reaction field 66b in the surface acoustic wave device 44 of the second embodiment (refer to FIG. 4) is removed and the piezoelectric substrate 58 is thereby exposed.

Except for the configuration of the peeled portion 80, the configuration of the surface acoustic wave device 76 is the same as the configuration of the surface acoustic wave device 44.

The reaction field 66b to which the piezoelectric substrate 58 is exposed is in an electrically opened state where the reaction field has amplitude and phase characteristics which are different from those of the reaction field 66a.

An output signal in a case where the reaction field 66a is electrically short-circuited only receives a mechanical reciprocal action.

Moreover, an output signal in a case where the reaction field 66b is electrically opened receives a physical reciprocal action (an electrical reciprocal action and a mechanical reciprocal action).

Accordingly, as a result of compensating the mechanical reciprocal actions of the output signals based on two the reaction fields 66a and 66b and of extracting the electrical reciprocal action, it is possible to determine a relative permittivity or an electrical conductivity of the measured object (for example, refer to "Development of Novel SAW Liquid Sensing System with SAW Signal Generator", Itsufumi, Hato and other two persons, TECHNICAL REPORT OF IEICE, THE INSTITUTE OF ELECTRONICS, INFORMATION AND COMMUNICATION ENGINEERS, 2003 February).

In the object characteristics measurement apparatus 78 of the third embodiment which is configured as described above, the same measured object is dropped on each of the reaction fields 66a and 66b, subsequently, each of the interdigitated electrodes 60a and 60b excites an elastic wave.

The processor 56 can determine the physical characteristics of measured object such as a dielectric constant or an electrical conductivity with a high level of accuracy based on the signal associated with the shear horizontal surface acoustic wave obtained from the reaction field 66a which is electrically short-circuited and the signal associated with the shear horizontal surface acoustic wave obtained from the reaction field 66b which is electrically opened.

In particular, in the first to third embodiments, an example is described where the groove (reflector) (30, 64) is a groove, the invention is not limited to this configuration.

Figure 7:
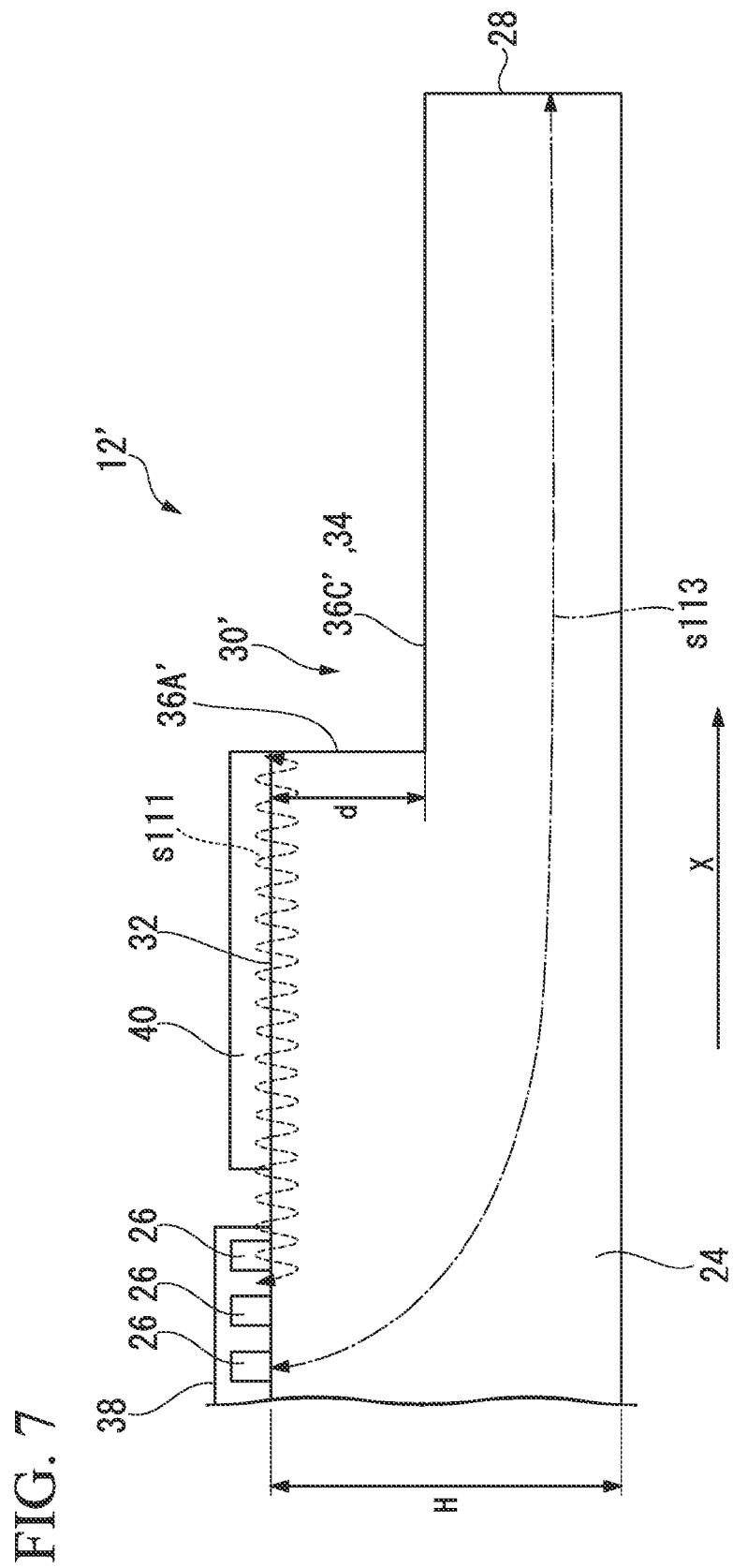
FIG. 7 is a cross-sectional view taken along the line IB-IB shown in an object characteristics measurement apparatus including a surface acoustic wave device.

FIG. 7 is a cross-sectional view taken along the line IB-IB showing an object characteristics measurement apparatus including a surface acoustic wave device 12'.

Particularly, FIG. 7 shows a cross-sectional view of FIG. 1A according to the first embodiment; however, the configuration shown in FIG. 7 is also similarly applicable to the second embodiment (FIG. 4) and the third embodiment (FIG. 5).

As shown in FIG. 7, a third surface 36C', which is disposed at a position different from the top surface of the piezoelectric substrate 24 (first surface) in the normal direction thereof, is formed at the surface acoustic wave device 12'

This third surface is continuously connected to the upper surface of the bulk wave propagator 34.

By means of this structure, a reflecting surface 36A' serving as a fourth surface is formed to connect an end of the first surface and an end of the third surface.

That is, the object characteristics measurement apparatus (10, 46, and 78) according to the invention only has the reflecting surface 36 (36A, 36', and 72) and may not have a surface 36B (refer to FIG. 6) which is provided parallel with the reflecting surface 36 (36A, 36', and 72).

According to such configuration, as similar to the first to third embodiments, since the shear horizontal surface acoustic wave s111 is reflected by the reflecting surface 36A' and the bulk wave s113 is reflected by the end 28, it is possible to separate the shear horizontal surface acoustic wave s111 from the bulk wave s113.

Consequently, the object characteristics measurement apparatus 10 can be obtained which includes a downsized and inexpensive surface acoustic wave device 12' that can determine physical characteristics of the measured object with a high level of accuracy.

<Fourth Embodiment>

Figure 8:
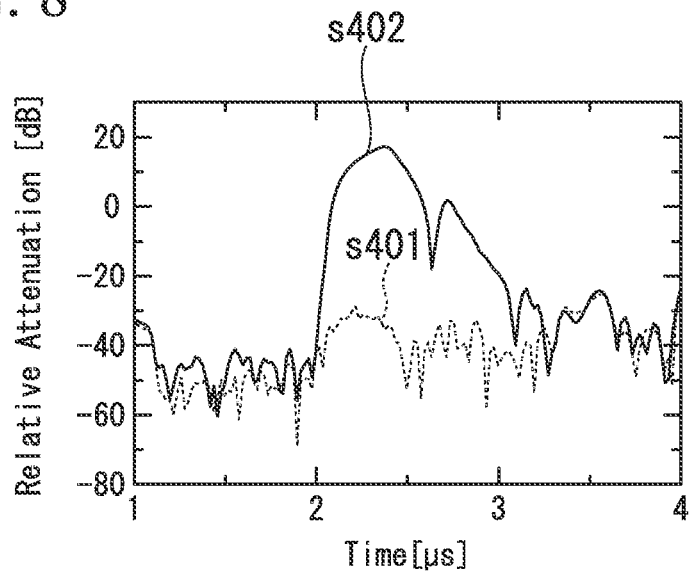
FIG. 8 is a chart showing an example of actual measured values in the case where a depth of the groove of the first embodiment of the invention is 0.06 mm.

FIG. 8 is a chart showing an example of actual measured values in the case where a depth d of the groove 30 of the first embodiment is 0.06 mm.

Figure 9:
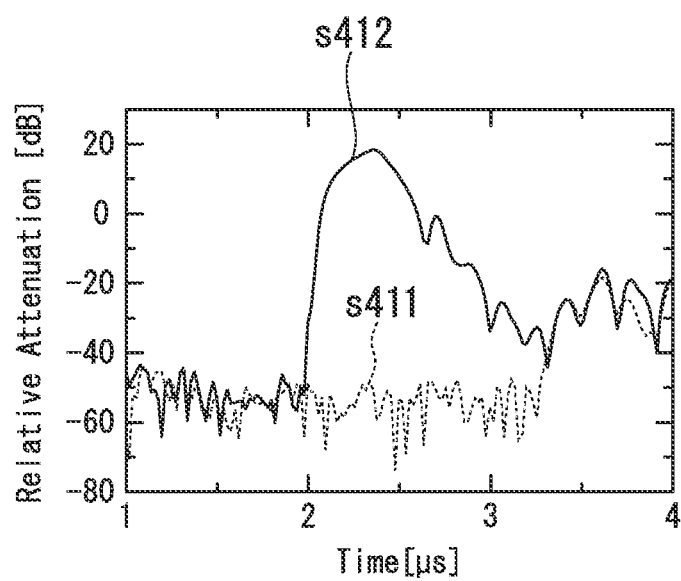
FIG. 9 is a chart showing an example of actual measured values in the case where a depth of the groove of the first embodiment of the invention is 0.01 mm.

FIG. 9 is a chart showing an example of actual measured values in the case where the depth d of the groove 30 of the first embodiment is 0.01 mm.

In FIGS. 8 and 9, the horizontal axis represents time and the vertical axis represents signal level.

FIGS. 8 and 9, curve lines s401 and s411 represent the characteristics of the signal level of a bulk wave with respect to a time thereof, and curve line s402 and s412 represent the characteristics of the signal level of a shear horizontal surface acoustic wave with respect to a time thereof.

As shown in FIG. 1B or 6, a bottom surface (third surface) of the groove 30 is formed substantially parallel to the lower surface of the piezoelectric substrate 24 in the first embodiment.

In the case where the depth d of the groove 30 is 0.06 mm as shown in FIG. 8, a level difference between the bulk wave s401 and the shear horizontal surface acoustic wave s402 between the time points of approximately 2 μs and approximately 3 μs is approximately 60 dB.

Next, in the case where the depth d of the groove 30 is 0.01 mm as shown in FIG. 9, a level difference between the bulk wave s411 and the shear horizontal surface acoustic wave s412 between the time points of approximately 2 μs and approximately 3 μs is approximately 70 dB.

As stated above, in the case where the depth d of the groove 30 is deeper than a predetermined depth, the signal level of the bulk wave increases.

The reason for this is that, the signal level of the bulk wave which is reflected by the reflecting surface 36 of the groove 30A and returns to the interdigitated electrode 26 as shown in FIG. 6 increases.

Consequently, in the case where the reflecting surface 36A satisfies the aforementioned relational expression (3), it is possible to increase a level difference between the bulk wave s401 and the shear horizontal surface acoustic wave s402.

However, even where the depth d of the groove 30 is 0.01 mm as shown in FIG. 9, the signal level of the bulk wave s401 increases after the time point of approximately 3 μs.

Here, the reason that the signal level of the bulk wave s401 increases after the time point of approximately 3 μs will be described.

Figure 10:
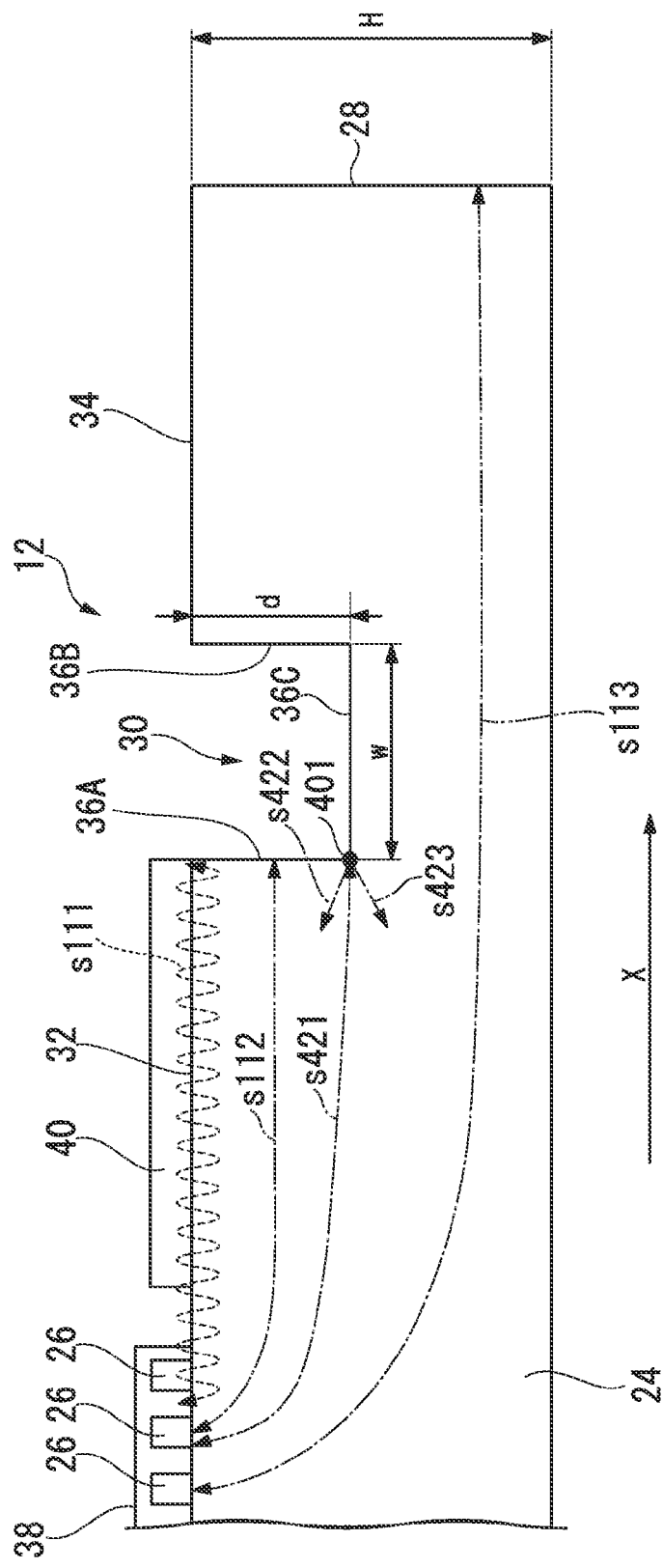
FIG. 10 is a view showing a configuration of a groove of a fourth embodiment of the invention.

FIG. 10 is a view showing the reflection at the end of the groove 30.

Identical reference numerals are used for the elements which are identical to that of FIG. 6, and the explanations thereof are omitted here.

In FIG. 10, the point 401 represents the end of the reflecting surface 36A (fourth surface) in the groove 30.

Additionally, the curve line s421 represents the bulk wave, the arrows s422 and s423 represent bulk waves which are newly generated at the end 401.

Furthermore, reference numeral 36B represents a surface that faces the reflecting surface 36A and is provided to be in contact with the bulk wave propagator 34, reference numeral 36C represents a bottom surface (third surface) of the groove 30.

As shown in FIG. 10, bulk waves s112 and s421 occur which are reflected by the reflecting surface 36 of the groove 30A and are other than the bulk wave s113 passing between the bottom surface 36C of the groove 30 and the lower surface of the piezoelectric substrate 24 and being reflected by the end (second surface) 28.

The bulk wave s421, that is to be reflected by the end 401 of the reflecting surface 36A, is not only reflected simply at the end 401 but also generates new bulk waves as shown by the arrows s422 and s423.

Since the bulk wave s422 and s423 which are newly generated in the above-described manner belatedly reaches the interdigitated electrode 26, the signal level of the bulk wave s401 increases after the time point of approximately 3 μs as shown in FIG. 9.

Consequently, as a result of suppressing the bulk waves that are newly generated at the end of the groove in the fourth embodiment, it promotes the separation of the bulk wave from the shear horizontal surface acoustic wave.

Figure 11:
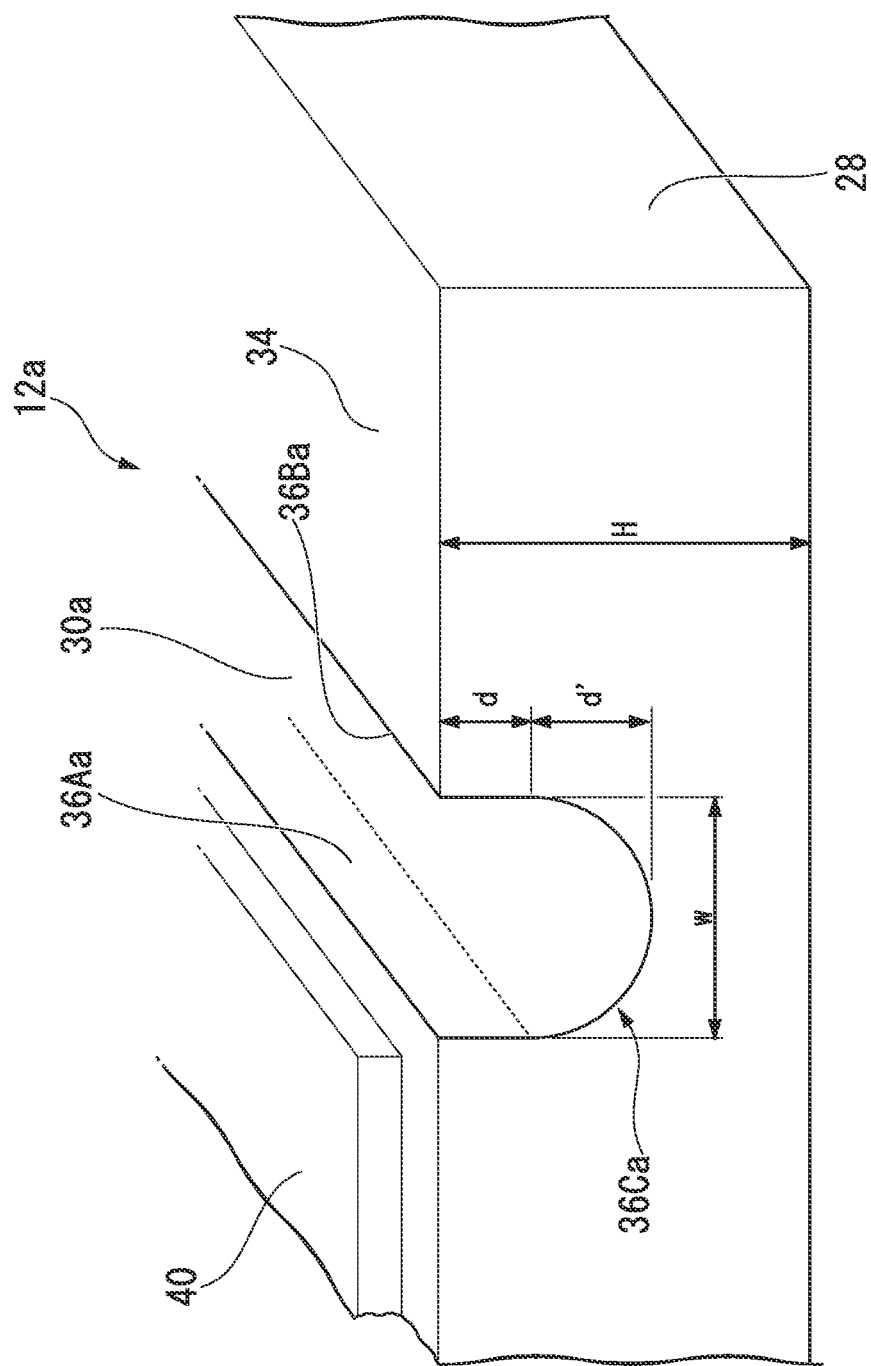
FIG. 11 is a view showing a configuration of a groove according to the fourth embodiment of the invention.

FIG. 11 is a view showing a configuration the groove 30a according to the fourth embodiment.

In FIG. 11, the direction in which the surface acoustic wave propagates is represented by the X-direction, a direction perpendicular to the direction in which the surface acoustic wave propagates is represented by the Y-direction, and the thickness direction of the piezoelectric substrate 24 is represented by the Z-direction.

Particularly, FIG. 11 is a view showing an example of the groove 30a of the fourth embodiment which is applied to the object characteristics measurement apparatus 10 of the first embodiment shown in FIG. 1A; however it is applicable to the object characteristics measurement apparatuses 46 and 78 of the second and third embodiments.

Additionally, H represents a thickness of the piezoelectric substrate 24 in the Z-direction.

As shown in FIG. 11, the groove (reflector) 30a has a side surface (fourth surface) 36Aa and a side surface 36Ba, each of which has a depth d in the Z-direction, and a semicircular curved surface which has, for example, a diameter of w (third surface) 36Ca (at least one portion of the third surface is a curved surface).

As similar to the first embodiment, a depth d of the side surface 36Aa is greater than or equal to $\lambda/2$ and less than or equal to H/2.

Additionally, as similar to the first to third embodiments, the side surface 36Ba may be formed substantially parallel to the side surface 36Aa.

A depth d' of the curved surface 36Ca in the Z-direction, for example, w/2.

Thus, the maximum total depth of the groove 30a is d+d'.

As mentioned above, the bottom surface 36Ca of the groove 30a of the surface acoustic wave device 12a does not has the shape that is substantially parallel to the lower surface of the piezoelectric substrate 24 such as the bottom surface 36C of the first to third embodiments (refer to FIG. 6) rather than has a curved surface.

Because of this, the position on the bottom surface 36Ca in the X-direction varies depending on the position thereon in the Z-direction.

The "the position in the X-direction varies depending on the position thereon in the Z-direction" means that, specifically, in the case where the coordinates of the bottom surface 36Ca are represented by the XZ plane, at least the coordinates of each position in X-direction or the Z-direction are different from each other such as position 1=(x1, z1), position 2=(x2, z2), . . . , .

Moreover, the groove 30a may be formed in a substantially semicircular shape by a projecting polygon.

In particular, in the fourth embodiment, the side surface 36Aa corresponds to the reflecting surface 36 of the first embodiment.

Figure 12:
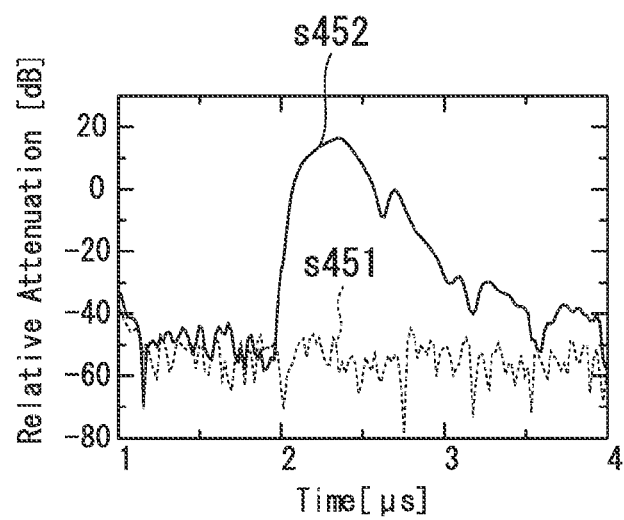
FIG. 12 is a chart showing an example of actual measured values in the case of provision of the groove shown in FIG. 11.

FIG. 12 is a chart showing an example of actual measured values in the case of providing the groove 30a shown in FIG. 11.

In FIG. 12, the horizontal axis represents time and the vertical axis represents a signal level.

Furthermore, a curve line s451 represents the characteristics of the signal level of a bulk wave with respect to a time thereof, and a curve line s452 represents the characteristics of the signal level of a shear horizontal surface acoustic wave with respect to a time thereof.

FIG. 12 shows actual measured values in the case where a depth d+d' of the groove 30a is 0.06 mm in FIG. 11.

In the case of the groove 30a as shown in FIG. 12, as similar to FIG. 9, a difference in level between the bulk wave s451 and the shear horizontal surface acoustic wave s452 is approximately 70 dB between the time points of approximately 2 μs and 3 μs.

The signal level of the bulk wave s401 increases after the time point of approximately 3 μs in FIG. 9; however, the level of the bulk wave s451 does not increase even after the time point of approximately 3 μs as shown in FIG. 12 in the fourth embodiment.

As stated above, even in the case where the measurement values shown in FIG. 12 are compared with both FIG. 8 showing the same depth of 0.06 mm and FIG. 9 having the side surfaces 36A and 36B showing a depth of 0.01 mm, a signal level of the bulk wave decreases.

Here, the reason will be explained that the signal level associated with the bulk wave can be reduced in the case of applying the groove 30a of the fourth embodiment to the object characteristics measurement apparatus.

As shown by FIG. 10, an end is provided on the surface at which a bulk wave is to be reflected, a new bulk wave is generated due to this end.

In the case where the bottom surface 36Ca that is continuously connected to the side surface 36Aa of the groove 30a is formed to have a curved surface as shown in FIG. 11, an end is not formed at a connection or the like between the side surface 36Aa and the bottom surface 36Ca.

Because of this, as shown in FIG. 11, as a result of forming the groove 30a as an example, a new bulk wave is not generated due to the end.

In the case of FIG. 11, a bulk wave is reflected by the bottom surface 36Ca in addition to the side surface 36Aa.

However, since the bottom surface 36Ca is a curved surface, the timings of the bulk wave that is reflected at this surface and is received by the interdigitated electrode 26 (refer to FIGS. 1A and 1B) are different from each other depending on, for example, the depth positions in the Z-direction.

That is, the bulk waves that are received by the interdigitated electrode 26 are distributed.

As a result, according to the fourth embodiment, a signal level associated with the bulk wave can be reduced even after the time point of approximately 3 μs as shown in FIG. 12.

As described above, the surface acoustic wave device 12a according to the fourth embodiment has the groove 30a, and the groove 30a has the side surface 36Aa, that is perpendicular to the XY plane and is similar to the groove 30 as described in the first to third embodiments, and the curved surface 36Ca serving as a bottom surface.

With this configuration, the surface acoustic wave device 12a of the object characteristics measurement apparatus of the fourth embodiment can improve the degree of separation of the shear horizontal surface acoustic wave from the bulk wave more than that of the first to third embodiments.

Consequently, the object characteristics measurement apparatus 10 which is provided with a downsized and inexpensive surface acoustic wave device 12a capable of determining physical characteristics of the measured object with a high level of accuracy and measures characteristics of a measured object can be obtained.

Next, a modified example of the configuration of a groove will be described.

Figure 13:
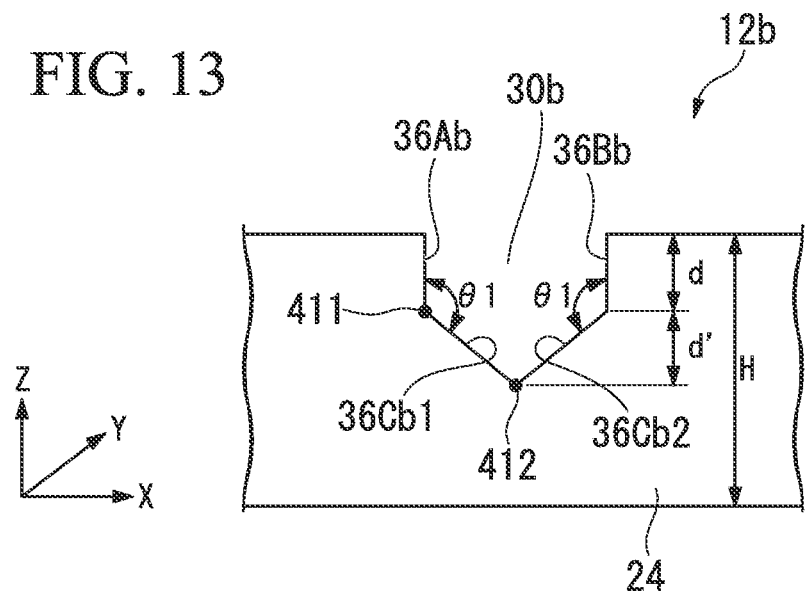
FIG. 13 is a modified example of a groove according to the fourth embodiment of the invention.
Figure 14:
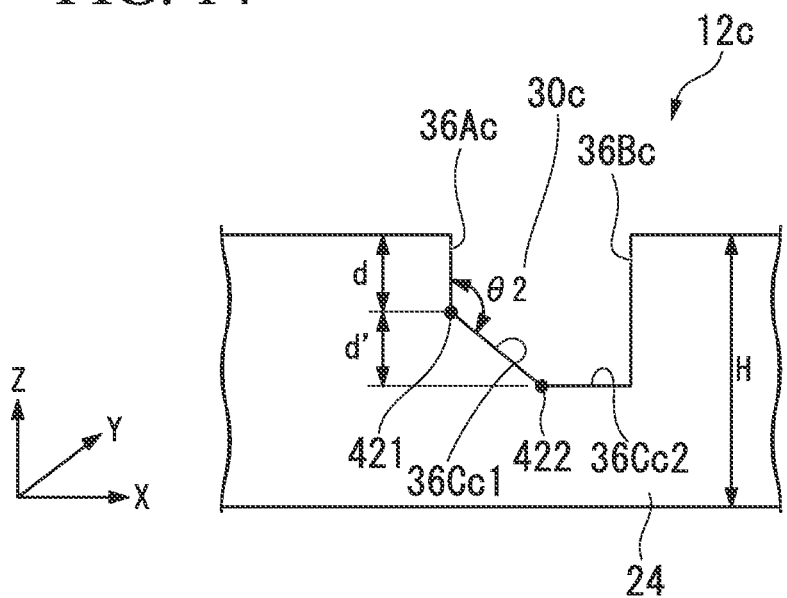
FIG. 14 is a modified example of a groove according to the fourth embodiment of the invention.

FIGS. 13 and 14 show modified examples of a groove according to the fourth embodiment.

Particularly, FIGS. 13 and 14 are cross-sectional views partially showing a surface acoustic wave device in the XZ plane.

In addition, the thickness of the piezoelectric substrate in the Z-direction is represented by H.

As shown in FIG. 13, a groove (reflector) 30b of a surface acoustic wave device 12b has a side surface 36Ab and a side surface 36Bb, each of which has a depth d in the Z-direction, an inclined face 36Cb1 (third surface), and an inclined face 36Cb2 (third surface).

The inclined face 36Cb1 is inclined with respect to the side surface 36Ab at an angle θ1 and is a flat surface in contact with the side surface 36Ab at one end (end 411, first end).

The inclined face 36Cb2 is inclined with respect to the side surface 36Bb at an angle θ1 and is a flat surface in contact with the side surface 36Bb at one end (first end).

The other end 412 (second end) of the inclined face 36Cb1 is in contact with the other end of the inclined face 36Cb2.

Furthermore, a depth d of the side surface 36Ab is greater than or equal to λ/2 and less than or equal to H/2 as similar to the first embodiment.

Moreover, the maximum depth of the groove 30b in the Z-direction is d+d'.

That is, the groove 30b has an inclined face and at least one portion of the inclined face is an inclination that is formed to be inclined with respect to the normal direction of the first surface of the piezoelectric substrate at a predetermined angle.

As stated above, the cross-sectional configuration of the groove 30b is a projected polygonal shape such that the shape protrudes from the superficial layer portion of the piezoelectric substrate 24 toward the inside of the piezoelectric substrate 24.

In other words, the above shape, which is surrounded by the side surface 36Ab, the side surface 36Bb, the inclined face 36Cb1, the inclined face 36Cb2, and the virtual line that is on the same plane as the top surface of the bulk wave propagator 34 and extends so as to close the groove 30b, is the projected polygonal shape (hereinbelow, refer to a projected polygonal shape).

In the embodiment, the cross-sectional configuration of the groove 30b is a pentagon.

Particularly, the case is described where the depths of the side surface 36Ab and the side surface 36Bb are the same as each other in the example shown in FIG. 13; however, the depths may be different from each other.

However, even in this case, it is only necessary for the depth d of the side surface 36Ab be greater than or equal to λ/2 and less than or equal to H/2.

Similarly, the angle θ1 formed between the side surface 36Ab and the inclined face 36Cb1 may be the same as or different from the angle θ1 formed between the side surface 36Bb and the inclined face 36Cb2.

As remarked above, the groove 30b is formed in a projected polygonal shape.

As shown in FIG. 14, a groove (reflector) 30c of the surface acoustic wave device 12c has a side surface 36Ac having a depth d in the Z-direction, a side surface 36Bc having a depth d+d' in the Z-direction, an inclined face 36Cc1 (third surface), and a bottom surface 36Cc2.

The inclined face 36Cc1 is inclined with respect to the side surface 36Ac at an angle θ2 and is a flat surface in contact with the side surface 36Ac at one end (end 421, first end).

One end of the bottom surface 36Cc2 is in contact with the inclined face 36Cc1 at the inclined face 36Cc1 (the other end 422, second end), the other end of the bottom surface 36Cc2 is in contact with the lower end of the side surface 36Bc, and the bottom surface 36Cc2 is parallel to the lower surface of the piezoelectric substrate 24.

The depth d of the side surface 36Ac is greater than or equal to λ/2 and less than or equal to H/2, which is similar to the first embodiment.

Moreover, the maximum depth of the groove 30c in the Z-direction is d+d'.

That is, the groove 30c has an inclined face and at least one portion of the inclined face is an inclination that is formed to be inclined with respect to the normal direction of the first surface of the piezoelectric substrate at a predetermined angle.

As stated above, the cross-sectional configuration of the groove 30c is a projected polygonal shape such that the shape protrudes from the superficial layer portion of the piezoelectric substrate 24 toward the inside of the piezoelectric substrate 24.

In other words, the above shape, which is surrounded by the side surface 36Ac, the side surface 36Bc, the inclined face 36Cc1, the bottom surface 36Cc2, and the virtual line that is on the same plane as the top surface of the bulk wave propagator 34 and extends so as to close the groove 30c, is the projected polygonal shape (hereinbelow, refer to a projected polygonal shape).

In the embodiment, the cross-sectional configuration of the groove 30c is a pentagon.

Particularly, the case is described where the groove 30c has the bottom surface 36Cc2 in the example shown in FIG. 14; however, it may not have the bottom surface 36Cc2.

In this case, the other end of the inclined face 36Cc1 may be in contact with the lower end of the side surface 36Bc.

As remarked above, the groove 30c is formed in a projected polygonal shape.

Next, propagation of a bulk wave in the groove having the configuration such as shown in FIGS. 13 and 14 will be described.

As shown in FIG. 13, the groove 30b has the end 411 and the end 412.

For this reason, new bulk wave are generated due to such ends.

Similarly, as shown in FIG. 14, the groove 30c has the end 421 and the end 422.

For this reason, new bulk wave are generated due to such ends.

However, the groove 30b of the fourth embodiment is different from the first to third embodiments (for example, FIG. 6) and has the inclined face 36Cb1 that is continuously connected to the side surface 36Ab having the depth d.

Similarly, the groove 30c of the fourth embodiment has the inclined face 36Cc1 that is continuously connected to the side surface 36Ac and has the depth d.

Consequently, a bulk wave is not only reflected by the aforementioned ends (411 and 412 or 421 and 422) but also reflected at each of positions on the inclined faces 36Cb1 and 36Cc1.

Similar to the bottom surface 36Ca shown in FIG. 11, the positions on the inclined faces 36Cb1 and 36Cc1 in the XZ plane are different from each other.

Because of this, in the embodiment, at time points different from each other, the interdigitated electrode 24 receives not only new bulk waves generated at the ends 411, 412, 421, and 422 but also each of bulk waves that are reflected at the positions.

Consequently, similar to the case where the bottom surface 36Ca is a curved surface, the bulk waves that are received by the interdigitated electrode 24 are distributed in a time direction.

For this reason, with the surface acoustic wave device 12b or 12c including the groove 30b or 30c shown in FIG. 13 or 14, it is possible to reduce a signal level associated with the bulk wave.

As described above, the fourth embodiment includes the bottom surface 36Ca serving as a curved surface or the inclined face (36Cb1 or 36Cc1) in addition to the side surfaces (36Aa, 36Ab, or 36Ac) having the depth d, of the groove (30 or 64) of the first to third embodiments.

With this configuration, similar to the first to third embodiments, the interdigitated electrode 24 receives a signal based on the shear horizontal surface acoustic wave reflected by the side surface (36Aa, 36Ab, or 36Ac).

Additionally, the interdigitated electrode 24 receives signals based on the bulk waves that are reflected by the side surface (36Aa, 36Ab, or 36Ac), the bottom surface 36Ca, or the inclined face (36Cb1 or 36Cc1), and the end 28.

In the above, the bulk waves that are reflected by the bottom surface 36Ca or the inclined face (36Cb1 or 36Cc1), and the end 28 are distributed and received.

Accordingly, even where the end 411 or the like is provided between the side surface 36Ab and the inclined face 36Cb1 as shown in FIG. 13, since the bulk waves can be dispersed, it is possible to reduce the influence of newly-generated bulk waves.

Because of this, according to the fourth embodiment, since it is possible to reduce a bulk wave to be less than that of the first to third embodiments, it is possible to separate the bulk wave from a shear horizontal surface acoustic wave.

As a result, in the fourth embodiment, by use of the shear horizontal surface acoustic wave which is separated from the bulk wave in this manner, it is possible to determine physical characteristics of the measured object with a high level of accuracy.

<Fifth Embodiment>

Figure 15:
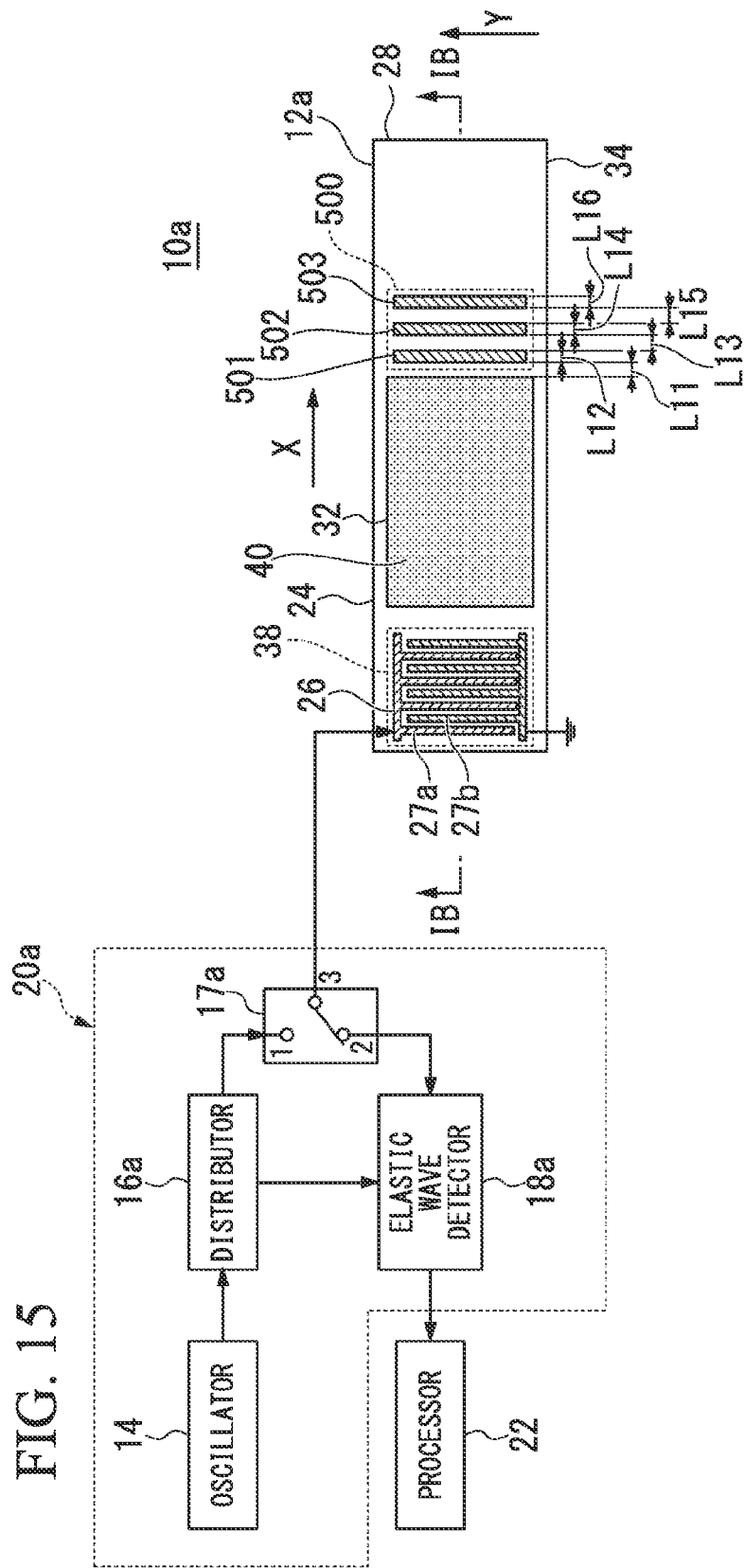
FIG. 15 is a plan view showing a configuration of an object characteristics measurement apparatus of a fifth embodiment of the invention including a surface acoustic wave device.

FIG. 15 is a plan view showing a configuration of an object characteristics measurement apparatus 10a of a fifth embodiment including the surface acoustic wave device 12a.

Figure 16A:
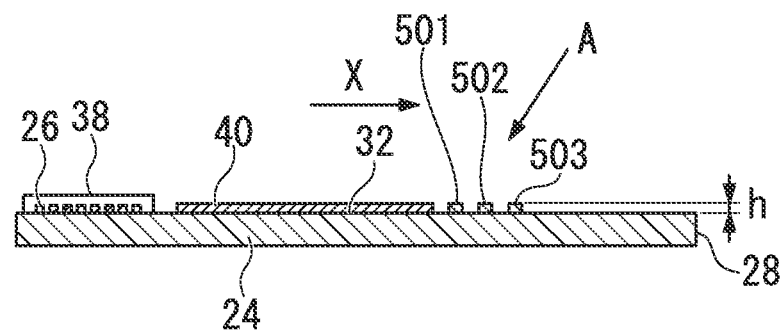
FIG. 16A is a cross-sectional view taken along the line IB-IB shown in a surface acoustic wave device shown in FIG. 15.

FIG. 16A is a cross-sectional view taken along the line IB-IB of the surface acoustic wave device 12a shown in FIG. 15A.

Figure 16B:
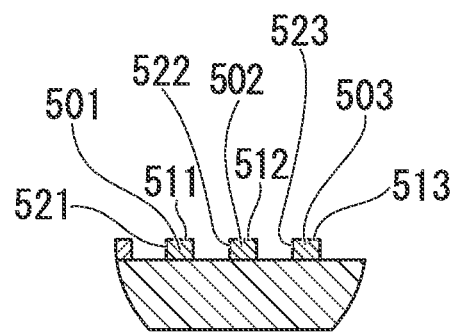
FIG. 16B is an enlarged cross-sectional view showing a portion represented by reference numeral A shown in FIG. 16A.

FIG. 16B is an enlarged cross-sectional view showing the portion indicated by reference numeral A of FIG. 16A and is an enlarged view of the portion including a reflector 500.

The object characteristics measurement apparatus 10a measures physical characteristics of the measured object.

The object characteristics measurement apparatus 10a is provided with: the surface acoustic wave device 12a; a measurement unit 20a configured by an oscillator 14a, a distributor 16a, a switch 17a, and an elastic wave detector 18a; and the processor 22 configured of a personal computer or the like.

The measurement unit 20a has a function that is the same as that of the measurement unit 20 of the first embodiment.

The surface acoustic wave device 12a includes: a piezoelectric substrate 24; an interdigitated electrode 26 that is formed on the piezoelectric substrate 24 and excites an elastic wave; the reflector 500 that is formed between the interdigitated electrode 26 and an end 28 of the piezoelectric substrate 24 in the propagation direction of an elastic wave (the X-arrow direction); a reaction field 32 which is formed between the interdigitated electrode 26 and reflectors 501 to 503 and in which the measured object is to be loaded; and a bulk wave propagator 34 through which a bulk wave propagates and which is formed between the reflectors 501 to 503 and the end 28.

The reflector 500 includes the reflectors 501 to 503.

From the viewpoint of provision of the reflectors 501 to 503, the surface acoustic wave device 12a of the embodiment is different from the first embodiment.

Additionally, in FIGS. 15, 16A, and 16B, the propagation direction of an elastic wave is represented by the X-direction, and a direction orthogonal to the propagation direction of the surface acoustic wave is represented by Y-direction.

The reflectors 501 to 503 are formed so as to extend from one end (first substrate edge) of the piezoelectric substrate 24 to the other end (second substrate edge) in the Y-direction.

The reflectors 501 to 503 have a wall having a height h which is substantially vertical to the top surface of the piezoelectric substrate 24 along which an elastic wave propagates (refer to FIGS. 16A and 16B).

The heights h of the walls of the reflectors 501 to 503 are determined depending on the wavelength $\lambda$ of the surface acoustic wave.

The reflector 501 is formed separately from the reaction field 32 at a length L11 in the X-direction.

Moreover, a width of the reflector 501 in the X-direction is L12.

The reflector 501 has a surface 511 (third surface) in the X-direction and a reflecting surface 521 (fourth surface) with a height h from the top surface of the piezoelectric substrate 24.

The reflector 502 is formed separately from the reflector 501 at a length L13 in the X-direction.

Moreover, a width of the reflector 502 in the X-direction is L14.

The reflector 502 has a surface 512 (third surface) in the X-direction and a reflecting surface 522 (fourth surface) with a height h from the top surface of the piezoelectric substrate 24.

The reflector 503 is formed separately from the reflector 502 at a length L15 in the X-direction.

Moreover, a width of the reflector 503 in the X-direction is L16.

The reflector 503 has a surface 513 (third surface) in the X-direction and a reflecting surface 523 (fourth surface) with a height h from the top surface of the piezoelectric substrate 24.

A surface acoustic wave propagates along the superficial layer portion of the piezoelectric substrate 24, is reflected by the surfaces 521 to 523 of the reflectors 501 to 503, respectively, thereafter, re-propagates along the reaction field 32, and is received by the interdigitated electrode 26.

In other cases, the lengths L11, L13, and L15 may be the same as or different from each other.

The widths L12, L14, and L16 may be the same as or different from each other.

Additionally, the heights h of the reflecting surfaces 521 to 522 of the reflectors 501 to 503 may be the same as or different from each other.

Particularly, FIGS. 15, 16A, and 16B illustrate the surface acoustic wave device 12a having three reflectors as examples; however, it is only necessary that the number of the reflectors be one or more.

Next, an example of processing according to the object characteristics measurement apparatus 10a will be described.

The processor 22 causes the switch 17a to carry out switching to connect the terminal 1 thereof to the terminal 3 thereof.

Therefore, the distributor 16a supplies a high-frequency oscillation signal to the interdigitated electrode 26 through the switch 17a.

In the interdigitated electrode 26, an elastic wave is excited in accordance with the supplied high-frequency oscillation signal.

The elastic wave propagates in the X-arrow direction along the reaction field 32 on which the measured object is dropped.

Of the elastic wave propagating along the reaction field 32, a shear horizontal surface acoustic wave that is a surface acoustic wave propagates along the superficial layer portion of the piezoelectric substrate 24, is reflected by the reflecting surfaces 521 to 523 of the reflectors 501 to 503, respectively, thereafter, re-propagates along the reaction field 32, and is received by the interdigitated electrode 26.

Additionally, a bulk wave propagates through the bulk wave propagator 34 inside the piezoelectric substrate 24 and the reaction field 32, and reaches the end 28 of the piezoelectric substrate 24.

Subsequently, the bulk wave is reflected by the end 28, thereafter, re-propagates through the bulk wave propagator 34 and the reaction field 32, and received by the interdigitated electrode 26.

The processor 22 causes the switch 17a to carry out switching to connect the terminal 2 thereof to the terminal 3 thereof.

The surface acoustic wave and the bulk wave which are received by the interdigitated electrode 26 are converted into a surface acoustic wave signal and a bulk wave signal, thereafter, are supplied to the elastic wave detector 18a.

In particular, the elastic wave detector 18a performs detection using the surface acoustic wave signal which is due to reflection of the reflector 502 located at the center of, for example, three reflectors 501 to 503.

In the case where two or more reflectors are provided, the elastic wave detector 18a performs the detection using the surface acoustic wave signal which is due to reflection of the reflector located at the center of the reflectors 501 to 503.

In the case where the number of the reflectors is even number, for example, in the case where four reflectors (first reflector to fourth reflector) are provided, the elastic wave detector 18a may carries out the detection using the surface acoustic wave signal which is due to the second reflector or the third reflector which is located at the center of four reflectors.

As described above, in the object characteristics measurement apparatus 10a of the fifth embodiment, the surface acoustic wave propagates along the reaction field 32, is reflected by the reflecting surfaces (521 to 523) of the reflector 500, and is received by the interdigitated electrode 26; in contrast to this, the bulk wave propagates through the bulk wave propagator 34 from the reaction field, is reflected by the end 28 of the piezoelectric substrate 24, thereafter, is reflected by the interdigitated electrode 26 so as to be delayed by a predetermined amount of time longer than the surface acoustic wave.

Accordingly, a signal based on the bulk wave is separated from a signal based on the elastic wave by utilizing the delay time, and a signal associated with the surface acoustic wave can be extracted therefrom.

Consequently, based on the signal associated with the surface acoustic wave, it is possible to determine physical characteristics of the measured object with a high level of accuracy.

Particularly, in the explanation in the fifth embodiment, one interdigitated electrode 26 and one the reaction field 32 are provided; however, a plurality thereof may be provided as described in the second and third embodiments.

Even in the cases, for example, the reflector 500 may be applied instead of the groove 64 shown in FIG. 4 and the groove 64 shown in FIG. 5.

Moreover, FIGS. 16A and 16B illustrate, as an example, that the shapes of the surfaces 511 to 513 of the reflectors 501 to 503 are a substantially-flat surface with respect to the piezoelectric substrate 24; however, the present invention is not limited to this example.

The shapes of the surfaces 511 to 513 of the reflectors 501 to 503 may be the other shape, for example, a semicircle, an inclined face, or the like.

In addition, the invention is not limited to the above embodiments, and various modifications may be made without departing from the scope of the invention.

For example, similar to the case shown in FIG. 3, as a result of coating the grooves 64, which are formed in the surface acoustic wave device 44 of the second embodiment and the surface acoustic wave device 76 of third embodiment, with the resin 42, it is possible to determine physical characteristics of the measured object with a high level of accuracy even in cases where part of a measured object is dropped on the groove 64.

The invention claimed is:

1. An object characteristics measurement apparatus, comprising a surface acoustic wave device, the surface acoustic wave device comprising:

an interdigitated electrode that is formed on a first surface on a piezoelectric substrate for exciting an elastic wave and for receiving at least one reflection based on the elastic wave;

a reflector that has a third surface and a fourth surface between the interdigitated electrode and a second surface orthogonal to the first surface of the piezoelectric substrate in a propagation direction of the elastic wave, the third surface being formed at a position different from that of the first surface in a normal direction of the first surface, the fourth surface connecting an end of the first surface, which is formed perpendicular to the normal direction of the first surface, to the third surface;

a reaction field that is formed between the interdigitated electrode and the reflector, in which a measured object is to be loaded; and a propagator that is formed between the reflector and the second surface, wherein a surface acoustic wave is separated and extracted from a bulk wave, and characteristics of the measured object are determined based on the extracted surface acoustic wave, the surface acoustic wave propagating along the reaction field from the interdigitated electrode, the surface acoustic wave being reflected by the fourth surface of the reflector, the surface acoustic wave propagating along a surface of the piezoelectric substrate which is included in the elastic wave that is received by the interdigitated electrode, the bulk wave being reflected by the second surface of the piezoelectric substrate, the bulk wave propagating through an inside of the piezoelectric substrate which is included in the elastic wave that is received by the interdigitated electrode.

2. The object characteristics measurement apparatus according to claim 1, wherein
the reflector has a wall, and a height d of the wall thereof in a direction from the surface of the piezoelectric substrate toward the inside of the piezoelectric substrate is a value satisfying a relationship represented by the following formula.

$$\lambda/2 \leq d \leq H/2$$

$\lambda$: Wavelength of the elastic wave
H: Thickness of the piezoelectric substrate.

3. The object characteristics measurement apparatus according to claim 1, wherein
the interdigitated electrode includes a plurality of electrode fingers which is N pairs of electrode fingers (N is an integer greater than or equal to 1), and
a length L2 from the fourth surface of the reflector to the end of the piezoelectric substrate is a value satisfying a relationship represented by the following formula.

$$L2 \geq N \times \lambda/2$$

$\lambda$: Wavelength of the elastic wave
N: Number of a plurality of pairs of electrode fingers constituting the interdigitated Electrode.

4. The object characteristics measurement apparatus according to claim 1, wherein
the reflector has the third surface, and the third surface is parallel to the first surface of the piezoelectric substrate.

5. The object characteristics measurement apparatus according to claim 1, wherein
the reflector has the third surface, and at least one portion of the third surface is a curved surface.

6. The object characteristics measurement apparatus according to claim 1, wherein
the reflector has the third surface, and at least one portion of the third surface is an inclined face that is inclined with respect to a normal direction of the first surface of the piezoelectric substrate at a predetermined angle.

7. The object characteristics measurement apparatus according to claim 1, wherein
a resin fills the reflector without protruding above the first surface of the piezoelectric substrate.

8. The object characteristics measurement apparatus according to claim 1, wherein
a plurality of interdigitated electrodes are formed on the piezoelectric substrate in a direction perpendicular to the propagation direction of the elastic wave, and
a plurality of reaction fields, which correspond to the respective interdigitated electrodes are formed between the interdigitated electrodes and the third surface of the reflector.

* * * * *